US006964764B2

(12) United States Patent
Zimmerman et al.

(10) Patent No.: US 6,964,764 B2
(45) Date of Patent: *Nov. 15, 2005

(54) METHOD OF THROMBOLYSIS BY LOCAL DELIVERY OF REVERSIBLY INACTIVATED ACIDIFIED PLASMIN

(75) Inventors: Thomas P. Zimmerman, Raleigh, NC (US); Valery Novokhatny, Raleigh, NC (US); Kyle A. Landskroner, Mill Valley, CA (US); Gary J. Jesmok, Richmond, CA (US); Kathryn K. Taylor, Apex, NC (US)

(73) Assignee: Talecris Biotherapeutics, Inc., Research Triangle Park, NC (US)

( * ) Notice: Subject to any disclaimer, the term of this patent is extended or adjusted under 35 U.S.C. 154(b) by 199 days.

This patent is subject to a terminal disclaimer.

(21) Appl. No.: 10/143,157

(22) Filed: May 10, 2002

(65) Prior Publication Data

US 2003/0026798 A1 Feb. 6, 2003

Related U.S. Application Data

(63) Continuation of application No. PCT/US00/31115, filed on Nov. 13, 2000, which is a continuation-in-part of application No. 09/438,331, filed on Nov. 13, 1999, now Pat. No. 6,355,243.

(51) Int. Cl.[7] .......................... A61K 38/48; C12N 9/72; C12N 9/68
(52) U.S. Cl. ...................... 424/94.64; 435/215; 435/217
(58) Field of Search ...................... 424/94.64; 435/215, 435/217

(56) References Cited

U.S. PATENT DOCUMENTS

| | | | |
|---|---|---|---|
| 3,136,703 A | 6/1964 | Singher | |
| 3,434,929 A | 3/1969 | Buck et al. | |
| 3,950,513 A | 4/1976 | Jensen | |
| 4,082,612 A | 4/1978 | Robbins et al. | |
| 4,115,551 A | 9/1978 | Lormeau et al. | |
| 4,177,262 A | 12/1979 | Lormeau et al. | |
| 4,259,448 A | 3/1981 | Nakamura et al. | |
| 4,361,652 A | 11/1982 | Uemura et al. | |
| 4,361,653 A | 11/1982 | Watanabe et al. | |
| 4,442,213 A | 4/1984 | Heber et al. | |
| 4,446,316 A | 5/1984 | Chazov et al. | |
| 4,462,980 A | 7/1984 | Diedrichsen et al. | |
| 4,663,146 A | * 5/1987 | Morser et al. | 424/1.41 |
| 4,774,087 A | * 9/1988 | Wu et al. | 424/94.64 |
| 4,908,204 A | 3/1990 | Robinson et al. | |
| 5,024,829 A | * 6/1991 | Berger et al. | 424/1.49 |
| 5,096,637 A | 3/1992 | DiLeo et al. | |
| 5,165,912 A | * 11/1992 | Selmer et al. | 424/1.53 |
| 5,237,050 A | 8/1993 | Boyle et al. | |
| 5,288,489 A | 2/1994 | Reich et al. | |
| 5,290,692 A | 3/1994 | Suzuki et al. | |
| 5,304,383 A | 4/1994 | Eibl et al. | |
| 5,328,996 A | 7/1994 | Boyle | |
| 5,371,007 A | 12/1994 | Linnau et al. | |
| 5,407,673 A | * 4/1995 | Reich et al. | 424/94.64 |
| 5,472,692 A | 12/1995 | Liu et al. | |
| 5,728,674 A | 3/1998 | Sprecher et al. | |
| 5,767,269 A | * 6/1998 | Hirsh et al. | 536/55.3 |
| 5,776,452 A | 7/1998 | Eibl et al. | |
| 5,879,923 A | 3/1999 | Yago et al. | |
| 6,139,819 A | 10/2000 | Unger et al. | |
| 6,207,066 B1 | 3/2001 | Trese et al. | |

FOREIGN PATENT DOCUMENTS

| | | |
|---|---|---|
| CN | 1 167 823 A | 12/1997 |
| EP | 0 399 321 A2 | 11/1990 |
| GB | 904478 | 8/1962 |
| JP | 0207 8633 | 3/1990 |
| JP | 09 065895 A | 3/1997 |
| RO | 103 682 A | 12/1991 |
| WO | WO 87/06836 A | 11/1987 |
| WO | WO 93/15189 A | 8/1993 |
| WO | WO 95 04077 A1 | 2/1995 |

OTHER PUBLICATIONS

Robbins, KC et al., Journal of Biological Chemistry (1963), 238: 952–62. Purification of human plasminogen and plasmin by gel filtration on Sephadex and chromatography on Diethylaminoethyl–Sephadex.*

Dupe, RJ et al., Thrombosis and Haemostasis (1981), 51(2): 248–253. Acyl–enzymes as thromblytic agents in dog models of venous thrombosis and pulmonary embolism.*

Beathard, GA. Kidney International (1994), 45:1401–1406. Mechanical versus pharmacomechanical thrombolysis for the treatment of thrombosed dialysis access grafts.*

Abe, T. Proc. Intern. Cong. Hematol. (1962), 3: 1587–39. Fibirinolytic influence of monocarboxylic acids and some other substances.*

Kline, D.L., "The Purification and Crystallization of Plasminogen (Profibrinolysin)," Journal of Biological Chemistry, 204: 949–955 (1953).

Supplementary Partial European Search Report (EP 00 99 1956, dated Dec. 17, 2004).

Jespersen, J., et al., "The autodigestion of human plasmin follows a bimolecular mode of reaction subject to product inhibition," Thromb. Res. 41(3):395–404 (1986).

(Continued)

Primary Examiner—Michele Flood
(74) Attorney, Agent, or Firm—Womble Carlyle Sandridge & Rice, PLLC

(57) ABSTRACT

Methods of thrombolysis that allow the use of a fibrinolytic composition comprising reversibly inactivated acidified plasmin and the localized delivery of the plasmin to a vascular thrombotic occlusion are disclosed. Further disclosed is a method for administering a therapeutic dose of a fibrinolytic composition substantially free of plasminogen activator to a human or animal having a vascular thrombotic occlusion. The fibrinolytic composition includes a reversibly inactivated acidified plasmin substantially free of plasminogen activator. Intravascular catheter delivery of the fibrinolytic composition directly into or in the immediate vicinity of the thrombus is disclosed to minimize the systemic degradation of fibrin while retaining the maximum plasmin activity against the thrombus.

35 Claims, 18 Drawing Sheets

OTHER PUBLICATIONS

Johnson, A.J., et al., "Assay methods and standard preparations for plasmin, plasminogen and urokinase in purified systems, 1967–1968," *Thromb. Diath. Haemorrh.*, 21(2):259–72 (1969).

Kirkwood, T.B.L., et al., "A standard for human plasmin," *Thromb. Diath. Haemorrh.*, 34(1):20–30 (1975).

Kline, D.L. and J.B. Fishman, Preparation, Stabilization and Some Properties of Purified Human Plasmin, *Thromb. Diath. Haemorrh.*, 11:75–84 (1964).

Ling, C.M., et al., "Mechanism of formation of bovine plasminogen activator from human plasmin," *J. Biol. Chem.*, 240(11):4213–8 (1965).

Nahum, L.H., et al., "Fibrinolysis. II. Evaluation of enzymatic thrombolysis: Experiments with plasmin preparations in arterial, venous thrombosis," *Conn. Med.* 24:139–46 (1960).

Robbins. K.C., et al., "The peptide chains of human plasmin. Mechanism of activation of human plasminogen to plasmin," *J. Biol. Chem.*, 242(10):2333–42 (1967).

Sgouris, J,T, et al. "The preparation of human fibrinolysin (plasmin)," *Vox Sang.*, 5:357–76 (1960).

Summaria, L., et al., "Recombinant human Lys–plasmin and the Lys–plasmin–streptokinase complex," *J. Biol. Chem.*, 254(14):6811–4 (1979).

Summaria, L., et al., "The specific mechanism of activation of human plasminogen to plasmin," *J. Biol. Chem.*, 242(19):4279–83 (1967).

Ueshima, S., et al., "Stabilization of plasmin by lysine derivatives," *Clin. Chim. Acta.*, 245(1):7–18 (1996).

Wohl, R.C., et al., "Kinetics of activation of human plasminogen by different activator species at pH 7.4 and 37°C," *J. Biol. Chem.*, 255(5):2005–13 (1980).

Wohl, R.C., et al., "Steady state kinetics of activation of human and bovine plasminogens by streptokinase and its equimolar complexes with various activated forms of human plasminogen," *J. Biol. Chem.*, 253(5):1402–7 (1978).

Binder, B.R., et al., "Purification and Characterization of Human Vascular Plasminogen Activator Derived from Blood Vessel Perfusates," *Journal of Biological Chemistry*, 254(6): 1998–2003 (1979).

Castellino, F.J., et al., "Rabbit Plasminogen and Plasmin Isozymes," *Methods in Enzymology*, 45: 273–286 (1976).

Robbins, K.C., et al., "Human Plasminogen and Plasmin," *Methods in Enzymology*, 19: 184–199 (1970).

International Search Report (PCT/US03/34020, dated Jul. 27, 2004).

European Supplementary Partial Search Report (EP 00 97 8572, dated Jul. 16, 2004).

European Supplementary Partial Search Report (EP 00 99 1956, dated Jun. 1, 2004).

European Supplementary Partial Search Report (EP 00 99 0910, dated May 25, 2004).

Ambrus, C., et al., "Insolubilized Activators of the Fibrinolysin System," *J. Med.* 3:270–281 (1972).

Ambrus, J.L., et al., "Clinical Pharmacology of various types of fibrinolytic enzyme preparations," *Am. J. Cardiol.*, 6:462–475 (1960).

Amris, C.J., et al., "Effect of Plasmin Therapy on Blood Coagulation and on Plasma Proteins in Patients with Cancer," *Danish Medical Bulletin*, 11(5):141–145 (1964).

Amris, C.J., et al., "Turnover and Distribution of $^{131}$I-Labelled Procine Plasmin in Man and Dog," *Danish Medical Bulletin*, 11(5):146–152 (1964).

Anlyan, W., et al., "Experiences with Fibrinolysin in Peripheral Vascular Occlusive Disease," *Am. J. Cardiol.*, 6:507–512 (1960).

Barrett, A.J., et al., "The Electrophoretically 'Slow' and 'Fast' Forms of the α2–Macroglobulin Molecule," *Biochem. J.*, 181:401–418 (1979).

Boucek, R., et al., "Segmental Perfusion of the Coronary Arteries with Fibrinolysin in Man Following a Myocardial Infarction," *Am. J. Cardiol.*, 6:525–533 (1960).

Boyles, P.W., et al., "Comparative effectiveness of intravenous and intra–arterial fibrinolysin therapy," *Am. J. Cardiol.*, 6:439–446 (1960).

Castellino, F.J. and J.R. Powell, "Human Plasminogen," *Meth. Enzymology*, 80:365–378 (1981).

Collen, D., et al., "Thrombolysis with human extrinsic (tissue–type) plasminogen activator in rabbits with experimental jugular vein thrombosis. Effect of molecular form and dose of activator, age of the thrombus, and route of administration," *J. of Clin. Invest.*, 71(2):368–376 (1983).

Deutsch, D.G. and E.T. Mertz, "Plasminogen: purification from human plasma by affinity chromatography," *Science* 170:1095–1096 (1970).

Freitag, H., et al., "Lys–plasminogen as an Adjunct to Local Intra–arterial Fibrinolysis of Carotid Territory Stroke: Laboratory and Clinical Findings," *Neuroradiology*, 38:181–185 (1996).

Hedner, U., et al., "Effects of Porcine Plasmin on the Coagulation and Fibrinolytic Systems in Humans," *Blood*, 51(1):157–164 (1978).

Kitamoto, Y., et al., "A Femoral Vein Catheter with Immobilized Urokinase (UKFC) as an Antithrombotic Blood Access," *Trans. Am. Soc. Artif. Intern. Organs*, 33:136–139 (1987).

Larsen, V., "Fibrinolytic Enzyme in the Treatment of Patients with Cancer," *Danish Medical Bulletin*, 2(5):137–140 (1964).

Larson, V., et al., "Fibrinolytic Treatment with Activator-–Free Porcine Plasmin," *Scand. J. Clin. Invest. 18(Suppl. 89)*:34–73 (1966).

Lijnen, H.R., et al., "Activation of plasminogen by pro–urokinase," *J. Biol. Chem.*, 261(1):1253–1258 (1986).

Lippschutz, E.L., et al., "Controlled study of the treatment of coronary occlusion with urokinase–activated human plasmin," *Am. J. Cardiol.*, 16:93–98 (1965).

Moser, K., "Effects of Intravenous Administration of Fibrinolysin (Plasmin) in Man," *Circulation*, 20:42–55 (1959).

Mizutani et al. "Potential thrombolysis under selective infusion of autolotous plasmin (AP) solution," *Japanese Heart Journal*, 30(5):723–732 (1989).

Nilsson, T. and B. Wiman, "On the structure of the stable complex between plasmin and alpha–2–antiplasmin," *FEBS Lett.*, 142(1):111–114 (1982).

Novokhatny, V. et al. "Thrombolytic potential of locally delivered active plasmin (Pm): In vitro assessment and in vivo comparison with tPA in the rabbit jugular vein trombosis model," Blood, 92(10) Suppl. 2, Abstract 3400. (Nov. 15, 1998).

Robbins, K.C. and L. Summaria, "Plasminogen and Plasmin," *Meth. Enzymol.* 45:257–273 (1976).

Sherry, S., "The Origin of Thrombolytic Therapy," *J. Am. Coll. Cardiol.*, 14(4):1085–1092 (1989).

Verstraete, M., "The Fibrinolytic System: from Petri Dishes to Genetic Engineering," *Thrombosis and Haemostasis*, 74(1):25–35 (1995).

Wiman, B., "Affinity–chromatographic purification of human alpha 2–antiplasmin," *Biochem. J.*, 191(1):229–232 (1980).

* cited by examiner

METHOD OF THROMBOLYSIS BY LOCAL DELIVERY OF REVERSIBLY INACTIVATED ACIDIFIED PLASMIN

REFERENCE TO RELATED APPLICATION

This application is a continuation of International Application PCT/US00/31115 published in English on Nov. 13, 2000, which in turn is a continuation-in-part of U.S. patent application Ser. No. 09/438,331, filed Nov. 13, 1999 now U.S. Pat. No. 6,355,243.

FIELD OF THE INVENTION

The present invention relates generally to a method of thrombolysis using reversibly inactivated acidified plasmin that is substantially free of plasminogen activators and its local delivery of the acidified plasmin proximal to, or directly within, a thrombus. The therapeutic method is particularly applicable to the dissolution of thrombi wherever catheter-directed delivery is feasible.

BACKGROUND

Thrombotic disease is a major cause of morbidity and mortality in the modern world. Acute myocardial infarction and ischemic stroke are the first and third causes of death and disability in Western societies. Occlusive thrombosis results in loss of blood flow to vital organs producing local oxygen deprivation, cell necrosis and loss of organ function. There are major benefits to the rapid destruction of a thrombus, resulting in early re-canalization: it prevents cell death, reduces infarct size, preserves organ function, and reduces early and late mortality. Thrombolytic therapy is now administered to more than 750,000 patients per year worldwide, while many times that number could potentially benefit from such treatment.

Thrombolytic agents now used in the lysis of occlusive blood clots are plasminogen activators. Several different plasminogen activators are currently available for immediate clinical use and several new generation plasminogen activators are the subject of clinical testing: tissue plasminogen activator, tPA, and its second generation successor TNK-tPA, RETEPLASE™ (a deletion mutant of tPA), single chain urokinase-type plasminogen activator (scuPA, or pro-urokinase), urokinase (UK), streptokinase (SK), and anisoylated plasminogen streptokinase activator complex (APSAC). tPA, scuPA, and UK are normally to be found at low levels in humans. Streptokinase is a bacterial enzyme with a powerful thrombolytic activity. APSAC is an anisolated streptokinase-plasminogen complex. In all cases the plasminogen activators are capable of converting the zymogen plasminogen to the active protease plasmin. The advantage offered by tPA and scuPA (and, to a lesser degree, APSAC) is that their activation of plasminogen is fibrin specific; binding to fibrin is a prerequisite for their full proteolytic activity to be realized (Haber et al., 1989). Urokinase and streptokinase can activate plasminogen in the absence of fibrin. Such variation in the affinity for fibrin has important consequences as to the extent to which systemic bleeding occurs in animal models; these differences, however, have not been appreciated clinically.

Plasminogen activators universally exert their thrombolytic potential by activating circulating zymogen plasminogen into plasmin. Plasmin, the principle fibrinolytic enzyme in mammals is a serine protease with trypsin-like specificity that is derived from the inactive zymogen precursor plasminogen circulating in plasma. Plasminogen itself is a 791 amino acid polypeptide having an N-terminus glutamate residue. Plasminogen activators such as tissue plasminogen activator (tPA) or urokinase will cleave the single-chain plasminogen molecule, to produce active plasmin, at the $Arg^{561}$-$Val^{562}$ peptide bond. The resulting two polypeptide chains of plasmin are held together by two interchain disulfide bridges. The light chain of 25 kDa carries the catalytic center and is homologous to trypsin and other serine proteases. The heavy chain (60 kDa) consists of five triple-loop kringle structures with highly similar amino acid sequences. Some of these kringles contain so-called lysine-binding sites that are responsible for plasminogen and plasmin interaction with fibrin, $\alpha_2$-antiplasmin or other proteins.

The inherent problem with the therapeutic use of existing plasminogen activators such as tPA, UK and SK is bleeding complications associated with their use, including, for example, gastrointenstinal hemorrhage in up to 20% of patients. Intracranial hemorrhage, which is clinically the most serious, is a frequent and lethal side effect of current thrombolytic therapy, and occurs in approximately 1% of patients. The mechanism for bleeding is multifactorial and is believed to be due to unmasking of a vascular injury by lysis of a protective hemostatic plug and consequent loss of vascular integrity. This is combined with the systemic activation of the fibrinolytic system and its attendant depletion of clotting factors. The focus of much recent research has been on generating modified plasminogen activators that exhibit improved fibrin specificity; this was expected to reduce the amount of bleeding complications. In some cases, these novel activators tend to preserve the circulating levels of such clotting factors such as fibrinogen, Factors VIII and V, plasminogen, and $\alpha_2$-antiplasmin. They specifically target and bind to the fibrin molecules that reside in a thrombus, and will only act upon plasminogen when so bound. This has the result that plasminogen is cleaved to the active protease plasmin only in the vicinity of the thrombosis and the level of non-specific systemic cleavage of fibrin is reduced. However, the number of bleeding complications with these new plasminogen activators remains significant.

The clinical success for thrombolytic drugs such as tissue plasminogen activator (tPA), streptokinase and urokinase in reducing the extent of a thrombotic occlusion of a vascular vessel is established. Plasminogen activators have therefore become a treatment of choice in the management of acute myocardial infarction and some other thrombotic conditions. Nevertheless, various disorders, including myocardial infarction, occlusive stroke, deep venous thrombosis and peripheral arterial disease, remain a serious clinical problem and the known plasminogen activators currently used suffer from several limitations that impact their overall usefulness in the elimination of a thrombus. In myocardial infarction, vascular flow is restored within 90 minutes in approximately 50% of patients, while acute coronary re-occlusion occurs in roughly 10% of patients. Coronary recanalization requires on average 45 minutes or more. Residual mortality, principally due to intracerebral hemorrhage, is still at least 50% of the mortality level in the absence of thrombolysis treatment.

Most research in the area of thrombolytics has focused on improving the efficacy and fibrin specificity of existing plasminogen activators as well as finding new ones. Much of this effort has concentrated on targeting the plasminogen activators to the fibrin that forms the scaffold of a thrombus and to improve the pharmacokinetics of the activators when administered into the blood stream. This would allow their administration as bolus doses rather than as a continuous delivery that prolongs exposure of the patient to the active agent, and the accompanying risk of undesirable systemic hemorrhage.

Based on the results of Phase II clinical trials with targeted plasminogen activators such as TNK-tPA, vampire bat salivary plasminogen activator, however, the anticipated improvement in safety profiles of the new plasminogen activators have not been realized clinically following thrombolytic therapy. The percentage of moderate and major bleeding episodes, including intracranial hemorrhage and stroke, were comparable with the original unmodified tPA. The clogged arteries were not opened earlier, and the rate of re-occlusions remained unchanged. It appeared that the only benefit these activators have is the prolonged plasma half-life and the possibility of bolus administration.

Another problem with plasminogen activators is that they have limited efficacy in the treatment of long clots found in peripheral arterial occlusions (PAO). These thrombi are typically aged and can grow to a significant size. The average size of peripheral thrombi found both in the native arteries and grafts is 31±11 cm. Aged and retracted thrombi are deficient in plasminogen, which therefore limits the susceptibility of old thrombi to plasminogen activator-induced thrombolysis. It is quite common for a patient with a PAO to be treated for 24 hours or more with urokinase and even after this prolonged period not to have complete patency of the vessel. The problem is greater with the delivery of the existing thrombolytic agents via catheter directly into the interior of the thrombus where there are reduced levels of the plasminogen substrate.

A fundamentally different approach to avoid the problems associated with the systemic administration of a plasminogen activator to generate sufficient plasmin at the site of the thrombus, is to administer plasmin itself directly to the patient. This is because plasmin is ultimately the enzyme mediating thrombolysis initiated by plasminogen activators. Direct delivery of active plasmin directly into retracted thrombi would circumvent the inherent plasminogen deficiency of these thrombi and provide predictable, rapid and effective thrombolysis irrespective of plasminogen content.

Reich et al. in U.S. Pat. No. 5,288,489 discloses a fibrinolytic treatment that includes parenteral administration of plasmin into the body of a patient. The concentration and time of treatment were sufficient to allow active plasmin to attain a concentration at the site of an intravascular thrombus that is sufficient to lyse the thrombus or to reduce circulating fibrinogen levels. Reich et al., however, require generation of the plasmin from plasminogen immediately prior to its introduction into the body.

In contrast, Jenson in U.S. Pat. No. 3,950,513 discloses a porcine plasmin preparation that is asserted to be stabilized at low pH. The plasmin solution is neutralized before systemic administration to humans for thrombolytic therapy.

Yago et al. in U.S. Pat. No. 5,879,923 discloses plasmin compositions useful as a diagnostic reagent. The compositions of Yago et al. consist of low concentrations of plasmin at a neutral pH and an additional component that may be 1) an oligopeptide comprising at least two amino acids, or 2) at least two amino acids, or 3) a single amino acid and a polyhydric alcohol.

Plasmin represents a second mechanistic class of thrombolytic agents, distinct from the class of plasminogen activators. Although plasmin had been investigated as a potential thrombolytic agent, numerous technical difficulties have prevented effective clinical use of this fibrinolytic enzyme. These difficulties included the challenge of preparing pure plasmin that is free of all functional traces of the plasminogen activator used to generate plasmin from the inactive precursor, plasminogen. The thrombolytic activity of these earlier plasmin preparations was eventually attributed to the presence of contaminating plasminogen activators rather than to plasmin itself. The contaminating plasminogen activators, however, also triggered systemic bleeding at sites other than at the targeted thrombus. An additional drawback of streptokinase used for plasmin preparations is that its presence in a preparation of plasmin often causes adverse immune responses including fever and anaphylactic shock.

The most important limitation to the clinical use of plasmin is that, as a serine protease with broad specificity, it is highly prone to autodegradation and loss of activity at physiological pH. This provides severe challenges to the production of high-quality stable plasmin formulation suitable for prolonged periods of storage prior to use, and to safe and effective administration of plasmin to human patients suffering from occlusive thrombi.

What is needed, therefore, is a method of administering a stable form of active plasmin that is substantially free of plasminogen activators and which is active upon encountering a targeted vascular thrombotic occlusion.

What is also needed is a method of lysis of thrombi that directly delivers an activatable form of active plasmin via a catheter into the interior of the thrombus.

What is further needed is a method of thrombolysis in which an administered thrombolytic agent is restricted to the thrombotic site and which exhibits reduced systemic, and especially intracranial, hemorrhage.

These and other objectives and advantages of the invention will become fully apparent from the description and claims that follow or may be learned by the practice of the invention.

SUMMARY OF THE INVENTION

This invention relates to the discovery that thrombolytic therapy can be improved by the administration of reversibly inactivated acidified plasmin directly into, or proximal to, a thrombus. Purified plasmin is unstable at physiological pH due to autodegradation and, therefore, plasmin has not been readily available for therapeutic administration. The present invention provides a method of administering a therapeutic dose of a fibrinolytic composition to a human or animal having a vascular thrombotic occlusion, comprising administering a therapeutic dose of a pharmaceutically acceptable reversibly inactivated acidified fibrinolytic composition substantially free of plasminogen activator. The present invention further provides a method of administering a therapeutic dose of an reversibly inactivated acidified fibrinolytic composition comprising plasmin and a pharmaceutically acceptable acidified carrier, wherein the pharmaceutically acceptable carrier has a low buffering capacity.

The present invention also provides a method of administering a therapeutic dose of a reversibly inactivated acidified fibrinolytic composition, wherein the fibrinolytic composition comprises plasmin and a pharmaceutically acceptable acidified carrier, wherein the pharmaceutically acceptable acidified carrier comprises water and a pharmaceutically acceptable acid selected from the acid forms of carboxylic acids, amino acids or other compounds having a low buffering capacity and the acidified carrier has a pH less than about 4.0.

The present invention provides a method of administering a therapeutic dose of a reversibly inactivated acidified plasmin and a pharmaceutically acceptable acidified carrier, further comprising a pharmaceutically acceptable stabilizer such as, but not limited to, a sugar or a polyhydric alcohol.

In one aspect of the present invention, the fibrinolytic composition comprises a reversibly inactivated acidified serine protease substantially free of its respective activator, a low buffering capacity buffer, and optionally, a stabilizing agent. Such serine proteases include trypsin, chymotrypsin, pancreatic elastase II, cathepsin G, prostate-specific antigen, leukocyte elastase, chymase, tryptase, acrosin, human tissue kallikrein, and plasmin. Plasmin includes Glu-plasmin, Lys-plasmin, derivatives and modified or truncated variants thereof, including, but not limited to, midi-plasmin, mini-plasmin, or micro-plasmin.

The methods of the present invention comprise acidic conditions and stabilizers that render the plasmin stable for storage. The plasmin used in the present invention is obtained by activating plasminogen, and is isolated and stored in an acidified solution having a pH of less than about 4 to provide a stable formulation of plasmin. The fibrinolytic composition of the present invention may be lyophilised and is substantially free of plasminogen activator. The low buffering capacity of the plasmin composition allows rapid titration to a physiological pH when administered to a thrombus or serum. Acidified plasmin is rapidly neutralized and activated when administered in a low buffering capacity solution directly to the clot site for thrombolytic therapy.

Additional objects, features, and advantages of the invention will become more apparent upon review of the detailed description set forth below when taken in conjunction with the accompanying drawing figures, which are briefly described as follows.

DETAILED DESCRIPTION OF THE INVENTION

Figure 1:
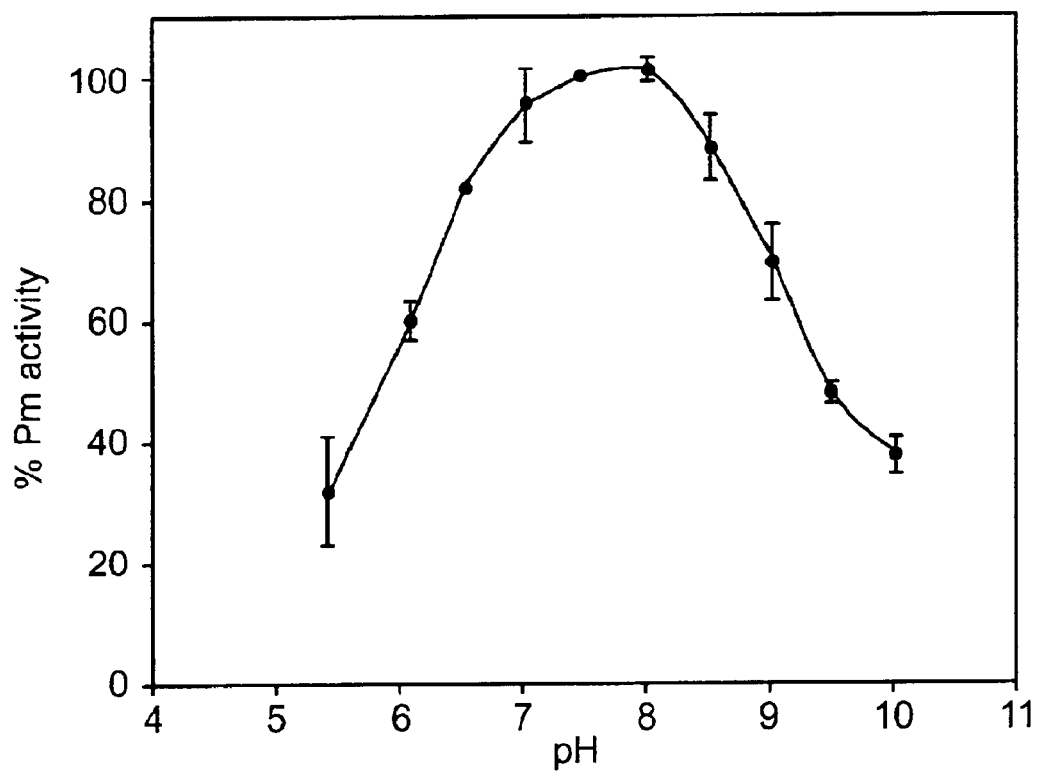
FIG. 1 illustrates the pH dependence of plasmin activity as measured with the chromogenic substrate S2251.

A full and enabling disclosure of the present invention, including the best mode known to the inventors of carrying out the invention, is set forth more particularly in the remainder of the specification, including reference to the Examples. This description is made for the purpose of illustrating the general principles of the invention and should not be taken in the limiting sense.

The present invention addresses the need for a method of thrombolysis that allows the use of a fibrinolytic composition comprising reversibly inactivated acidified plasmin and the localized delivery of the plasmin to a thrombotic occlusion. The invention provides a method for administering a therapeutic dose of a fibrinolytic composition to a human or animal having a thrombotic occlusion, comprising administering parenterally to the human or animal a therapeutic dose of a pharmaceutically acceptable reversibly inactivated acidified fibrinolytic composition substantially free of plasminogen activator, allowing the administered fibrinolytic composition to interact with the thrombotic occlusion, monitoring the level of vascular flow of the human or animal, and repeating these steps until a pre-selected level of vascular flow is attained. The method of the invention further provides for the use of a fibrinolytic composition comprising an reversibly inactivated acidified plasmin substantially free of plasminogen activator in a low buffering capacity buffer. The method also provides for the intravascular catheter direct delivery of the fibrinolytic composition into or in the immediate vicinity of the thrombus, thereby minimizing the systemic degradation of fibrin while retaining the maximum plasmin activity against the thrombus.

With the escalating use of arterial and venous catheters in the clinics, local delivery of reversibly inactivated acidified plasmin in close proximity to, or actually into, a thrombus offers an attractive therapeutic opportunity for thrombolysis. Being an active serine protease, plasmin is a direct thrombus dissolving agent, in contrast to plasminogen activators that require the presence of the zymogen plasminogen in the vicinity of the thrombus. Local catheter-directed thrombolytic therapy with active plasmin can be regulated to achieve localized total thrombolysis, and plasmin has the potential to be a safer thrombolytic agent because the lower dosage required for local delivery may significantly reduce bleeding complications frequently associated with high dose thrombolytic therapy induced by plasminogen activators. Any spillage of plasmin from the immediate vicinity of the thrombus site will be rapidly neutralized by circulating $\alpha_2$-antiplasmin.

There are several technical challenges associated with plasmin purification, and storage, as well as with its therapeutic use and delivery. Plasmin is an active serine protease and is subject to autodigestion and inactivation at physiological pH. Plasmin degradation, unfortunately, is also most evident in the pH range required for in vivo thrombolysis.

The fibrinolytic composition, as incorporated into the present invention, includes the maintenance of the plasmin in an acidic buffer during purification, as well as its formulation in an acidified carrier having a pharmaceutically acceptable low buffering capacity buffer, thereby providing a reversibly inactivated acidified plasmin-containing fibrinolytic composition substantially free of plasminogen activator. It is contemplated to be within the scope of the present invention for the fibrinolytic composition to be a lyophilized composition that may be reconstituted by the addition of a pharmaceutically acceptable carrier such as, but not limited to, water, physiological saline or any other solvent that will allow administration of the composition to a human or animal. Its efficacy in restoring vascular patency was demonstrated in in vitro assays and in an in vivo rabbit jugular vein thrombolysis model.

The term "reversibly inactivated" as used herein refers to an enzymic activity that is substantially free of activity under a specific set of conditions but will revert to an active form when transferred to another set of conditions.

The term "pharmaceutically acceptable carrier" as used herein refers to any carrier that is physiologically tolerated by a recipient human or animal, including, but not limited to, water, salt solutions, physiological saline, or any other liquid or gel in which a fibrinolytic agent such as plasmin may be dissolved or suspended. The "pharmaceutically acceptable carrier" may include any pharmaceutically acceptable compound that will give a plasmin solution having a pH below about 4.0 and which has low or zero buffering capacity.

The term "low buffering capacity buffer" as used herein refers to the amount of acid or base that a buffer can neutralize before the pH begins to change to an appreciable degree. As used herein a low buffering capacity buffer will be significantly pH adjusted by the addition of a small volume of an acid or base relative to the volume of the low buffering capacity buffer solution. This term is meant to include solutions acidified by strong acids including, but not limited to, hydrochloric acid, nitric acid or sulfuric acid, and which have no buffering capacity.

The term "physiological pH" as used herein refers to a pH between about pH 6.5 and 7.5, more typically between pH 7.1 to 7.5.

The term "thrombus" as used herein refers to a thrombus in a blood vessel or a device contacting blood (e.g. catheter devices or shunts). A thrombus may comprise fibrin and may further comprise, but is not limited to, platelets, erythrocytes, lymphocytes, lipid, serum constituents or any combination thereof. A "thrombus" may be, but is not limited to, an annular thrombus, ball thrombus, hyaline thrombus, mural thrombus, stratified thrombus or white thrombus.

The term "thrombotic occlusion" as used herein refers to a partial or total blockage of a vessel due to the formation of a thrombotic clot, wherein the thrombus comprises at least fibrin. The vascular vessel occluded may be, but is not limited to, a vein, artery, venule, arteriole, capillary, vascular bed or the heart and may be within any vascularized organ or tissue of the human or animal body. The thrombotic occlusion may also be of a catheter or other implant, including, but not limited to, prosthetic vessels and grafts of synthetic, human or animal origin, effectively blocked by an occlusion comprising fibrin.

The term "catheter device" as used herein refers to any catheter or tube-like device that may enter the body, and includes but is not limited to, an arterial catheter, cardiac catheter, central catheter, central venous catheter, intravenous catheter, balloon catheter devices peripherally inserted central catheter, pulmonary artery catheter or tunneled central venous catheter and arterio-venal shunts.

The term "pharmaceutically acceptable acidified carrier" as used herein refers to any pharmaceutically acceptable carrier that has been acidified to a pH below about 4.0. The "pharmaceutically acceptable acidified carrier" may comprise a low or zero buffering capacity buffer such as a carboxylic acid such as, but not limited to, formic, acetic, proprionic, butyric, citric, succinic, lactic or malic acids acidified to a pH below about 4.0 by the addition of an inorganic acid; or at least one amino acid such as, but not limited to, glycine, alanine, valine, isoleucine, threonine or glutamine, or at least one inorganic acid such as, but not limited to, sulfuric acid, hydrochloric acid, nitric acid or phosphoric acid or any combination thereof. It is contemplated to be within the scope of the present invention for the acid moiety of the pharmaceutical carrier to be at least one physiologically tolerated buffer, oligopeptide, inorganic or organic ion or any combination thereof that will maintain a pH in the pharmaceutically acceptable carrier below a value of about 4.0.

The term "carbohydrate" as used herein refers to any pharmaceutically acceptable saccharide or disaccharide such as, but not limited to, glucose, fructose, maltose or mannose, sugar alcohols including, but not limited to, sorbitol and mannitol, and polysaccharides such as, but not limited to, dextrins, dextrans, glycogen, starches and celluloses, or any combination or derivative thereof that are pharmaceutically acceptable to a human or animal.

The term "stabilizing agent" as used herein refers to at least one compound such as, but not limited to, glycerol, ascorbate, niacinamide, glucosamine, thiamine or inorganic salt such as, but not limited to, sodium chloride, potassium chloride, magnesium chloride or manganese chloride or any combination thereof that will increase the stability of a preparation of plasmin.

The term "reversibly inactivated acidified plasmin" as used herein refers to any catalytically active form of plasmin capable of proteolytically cleaving fibrin when under physiological conditions, but reversibly inactivated when placed at a pH between about pH 2.5 to about 4.0. The term "inactivated" as used herein refers to a total or substantial reduction in enzymatic activity compared to the activity at physiological pH. The term "active plasmin" as used herein refers to a plasmin under conditions where the plasmin is capable of proteolytically cleaving fibrin. The term "plasmin" includes, but is not limited to Glu-plasmin, Lys-plasmin, derivatives, modified or truncated variants thereof. The term "truncated variants" includes, but is not limited to, the midi-plasmin, mini-plasmin or micro-plasmin as disclosed in U.S. Pat. No. 4,774,087 incorporated herein by reference in its entirety.

The term "anti-coagulant" as used herein refers to any compound capable of inhibiting the formation of a thrombus including, but not limited to, hiruidin, heparin, thrombin inhibitors, platelet inhibitors, platelet aggregation inhibitors and any derivatives or combinations thereof.

The term "serine protease" as used herein refers to any serine protease capable of proteoytically cleaving fibrin including, but not limited to, plasmin, trypsin, chymotrypsin, pancreatic elastase II, cathepsin G, prostate-specific antigen, leukocyte elastase, chymase, tryptase, acrosin and human tissue kallikrein.

One limitation of current thrombolytic therapy with plasminogen activators is plasminogen availability surrounding or within a thrombus. The local delivery of a fibrinolytic agent to a thrombus now allows plasmin itself to be a potent therapeutic agent directly administered to a thrombus. In contrast to various plasminogen activators that are currently used as thrombolytics, direct localized thrombolytic therapy with plasmin can be intensified to whatever level is required to achieve clot lysis. This is because plasmin acts directly upon the fibrin polymer. Also, plasmin, when delivered directly into or adjacent to a thrombus, allows a lower effective dose to be administered with a concomittant reduction in the systemic hemorrhage typically associated with conventional thrombolytic therapy. Excess plasmin can also be rapidly inactivated by circulating $\alpha_2$-antiplasmin.

Highly purified active plasmin of the present invention was therefore prepared from plasminogen that had been purified from Cohn Fraction II+III. The purity of plasmin was greater than 95% and specific activity was in the range of 18–23 CU/mg. The plasmin preparations were substantially free of urokinase, or any other plasminogen activator, that had been used for the conversion of plasminogen into plasmin. The present invention also contemplates that plasmin substantially free of plasminogen activator may be prepared from any source including, but not limited to, mammalian serum, a recombinant plasminogen or a truncated plasminogen such as, but not limited to, the mini-plasminogen or micro-plasminogen as disclosed by Wu et al. in U.S. Pat. No. 4,774,087, incorporated herein by reference in its entirety.

The plasmin of the present invention was purified to substantially remove plasminogen activators by binding to a benzmidine-Sepharose chromatography column and eluted plasmin was collected and stored in an acidified pharmaceutically acceptable carrier having a low buffering capacity buffer. A low pH in the range of about 2.5 to about 4.0 significantly stabilized the plasmin, even when held at room temperature or greater. While not bound by any one theory, it is believed that at this low pH value the plasmin no longer has serine protease activity that would otherwise lead to autodegradation of the plasmin, as would be seen when plasmin is to be stored at the physiological pH of about 7.0–7.5.

When the reversibly inactivated acidified plasmin is administered, according to the methods of the present invention, directly into a thrombus or proximal thereto, the reversibly inactivated acidified plasmin in the low or zero buffering capacity buffer encounters the serum buffering capacity at the physiological pH of about 7.4. The low buffering capacity of the pharmaceutically acceptable carrier is neutralized, whereupon the plasmin reverts to its active state and proteolytically digests the fibrin of the thrombus.

By initially employing a method of plasmin preparation that renders plasmin proteolytically inactive until administered into, or immediately adjacent to, a thrombus, and which is also substantially free of any plasminogen activator, the likelihood of inducing undesirable systemic hemorrhage is diminished. Excess administered plasmin is rapidly inactivated by circulating serum inhibitors such as $\alpha_2$-antiplasmin, and the relatively stable plasminogen activators that would otherwise circulate to induce distal fibrinolysis are substantially absent.

Acidified plasmin may be readily stored in pharmaceutically acceptable carriers having a low or zero buffering capacity such as, but not limited to, aqueous 5 mM glycine. Any pharmaceutically acceptable ion may be used, singularly or in combination, if a pH is in the range of about 2.5–4.0. Typically, reversibly inactivated acidified plasmin has been maintained at a pH of 3.1–3.5. The pharmaceutically acceptable acidic ions incorporated in the carrier to maintain a low pH may be selected from oligopeptides, at least one amino acid, or organic or inorganic acids or a combination thereof. Stabilization may be further enhanced by the inclusion of at least one pharmaceutically acceptable compound that may be, but is not limited to a carbohydrate.

A description of the method of treating a thrombotic occlusion in a patient using a therapeutically effective dose of the low-pH plasmin compositions of the present invention is disclosed in U.S. patent application Ser. No. 10/143,112, entitled "Reversibly Inactivated Acidified Plasmin", commonly assigned and filed contemporaneously with the instant application, and is incorporated herein by reference in its entirety.

Additionally, a process for producing the reversibly inactivated acidified plasmin composition of the instant invention is disclosed in U.S. patent applicatio Ser. No. 10/143, 156, entitled "Process for the Production of a Reversibly Inactivated Plasmin Composition", commonly assigned and filed contemporaneously with the instant application, and is incorporated herein by reference in its entirety.

The administration of the plasmin composition can be by any method that will deliver the plasmin as a bolus or as a prolonged infusion directly into a thrombus, or to a site only a short distance proximal to the thrombus, whereupon it can rapidly encounter the thrombus. By minimizing this distance to the thrombus or by directly administering into the clots, plasmin exposure to plasmin inhibitors in the serum lying between the delivery needle or catheter and the thrombus is reduced. The present invention contemplates that the reversibly inactivated acidified plasmin may be delivered to the thrombus by a catheter. The present invention further contemplates that a cannulated needle, such as, but not limited to a syringe needle, may be used to inject the reversibly inactivated acidified plasmin into a thrombus. It is, however, within the scope of the present invention for any means known to one of skill in the art, to locally administer a fluid to a specific location in a human or animal. Catheter delivery to a vascular or coronary thrombus further allows precision in placing the plasmin, especially within the thrombus. While the present invention provides methods of localized delivery of an reversibly inactivated acidified plasmin in a low buffering capacity buffer to a thrombus, it is within the scope of the present invention for delivery of the reversibly inactivated acidified plasmin composition thereof to a fibrin occlusion of a catheter implanted in a human or animal.

Using an in vitro $^{125}$I-fibrin-labeled thrombolysis assay, it was shown that plasmin was capable of dissolving thrombi in a dose-dependent manner. Fibrinolysis was enhanced by deletion of either $\alpha_2$-antiplasmin or $\alpha_2$-microglobulin in plasma surrounding the thrombus, as well as by the deletion of all inhibitors (i.e., in PBS). These results show that thrombolysis by plasmin is under very strict regulation by the endogenous plasmin inhibitors, and provides the basis for safer thrombolytic therapy.

The in vivo efficacy of reversibly inactivated acidified plasmin (1–3 mg/kg) in a low buffering capacity buffer directly administered locally to a thrombus via a catheter was compared with that of tPA (0.5 and 1.0 mg/kg) in the rabbit jugular vein thrombosis model. The rate of thrombolysis was monitored. In addition, the consumption of Factor VIII and fibrinogen, as well as cuticle bleeding time (CBT), were measured as indicators of the systemic lytic state. In comparison with 0.5 mg/kg of tPA, plasmin provided comparable or significantly better thrombolysis, with comparable consumption of Factor VIII and fibrinogen and similar CBT at 1 mg/kg dose. There was a significantly increased consumption and CBT with plasmin at 3 mg/kg.

When compared with 1 mg/kg of tPA, both plasmin and tPA provided very similar thrombolysis rates with significantly less consumption of fibrinogen at 3 mg/kg plasmin.

Thus, reversibly inactivated acidified plasmin can be effectively and safely stored and used as a thrombolytic agent during catheter-assisted local thrombolysis without neutralization before administration to a human or animal. Plasmin has comparable, if not superior, fibrinolytic activity compared to tPA, and the safety profile appears at least similar in this animal model of local thrombolytic delivery.

It is contemplated to be within the scope of the present invention that the reversibly inactivated acidified fibrinolytic enzyme may be, but is not limited to, plasmin, derivatives of plasmin such as truncated forms thereof including, but not limited to, mini-plasmin and micro-plasmin.

The present invention provides a method of administering a therapeutic dose of a fluid fibrinolytic composition preparation substantially free of plasminogen activators to the immediate vicinity of, or directly into, a thrombotic occlusion of a vascular vessel or an occluded catheter device. The invention further provides a method for delivering a therapeutic dose of a fluid reversibly inactivated acidified plasmin composition to a vascular thrombotic occlusion wherein the plasmin may be stabilized prior to administration at a pH of about 4.0. The present invention further provides a method for delivering a therapeutic dose of a fluid reversibly inactivated acidified plasmin in a low buffering capacity buffer directly into a vascular thrombotic occlusion, or thrombus, whereupon the plasmin composition reverts to a physiological pH that allows the plasmin to proteolytically cleave fibrin.

In one embodiment of the present invention, the method of the invention comprises the steps of identifying a human or animal having a thrombotic occlusion, administering to the human or animal a therapeutic dose of a pharmaceutically acceptable reversibly inactivated acidified fibrinolytic composition in a low buffering capacity buffer, allowing the administered fibrinolytic composition to interact with the vascular occlusion, monitoring the level of vascular flow of the human or animal; and repeating steps of administering the fibrinolytic composition until a pre-selected level of vascular flow is attained.

In another embodiment of the present invention, the reversibly inactivated acidified fibrinolytic composition comprises plasmin and a pharmaceutically acceptable acidified carrier having a low buffering capacity buffer.

In still another embodiment of the present invention, the pharmaceutically acceptable acidified carrier comprises water and at least one pharmaceutically acceptable acid, wherein the acid is an organic acid, which may be, but is not limited to, a carboxylic acid, an oligopeptide, an amino acid, or an inorganic acid and having a low or zero buffering capacity, and the acidified carrier has a pH less than about 4.0.

In yet another embodiment, the pharmaceutically acceptable acidified carrier comprises water and a pharmaceutically acceptable acid selected from the acid forms of formate, acetate, citrate, glycine, isoleucine, serine, threonine, glutamine, and alanine, wherein the acidified carrier has a pH less than about 4.0.

In a further embodiment, the pharmaceutically acceptable acid is the acid form of acetate or citrate.

In yet another embodiment, the pharmaceutically acceptable acid is the acid form of acetate.

In an embodiment of the method of the present invention, the reversibly inactivated acidified fibrinolytic composition has a pH of between about 2.5 and about 4.0. In another embodiment of the method of the present invention, the fibrinolytic composition has a pH of about 3.7.

In other embodiments of the method of the present invention, the plasmin is in the concentration range of between about 0.01 mg/ml to about 50 mg/ml. In one embodiment of the method of the present invention the plasmin is in the concentration range of between about 0.1 mg/ml to about 10 mg/ml.

In further embodiments of the method of the present invention, the acidic ion is in the concentration range of between about 1 mM to about 500 mM. In one embodiment of the method of the present invention, the acidic ion is in the concentration range of between about 1 mM and 50 mM.

Embodiments for practicing the method of the present invention further comprise a physiologically acceptable plasmin stabilizer, wherein the carbohydrate is selected from glucose, maltose, mannitol, sorbitol, sucrose, lactose or trehalose, wherein the sugar has a concentration in the range of about 0.2% w/v to about 20% w/v. In one embodiment, the sugar is glucose and the concentration thereof is about 20%.

Embodiments of the method of the present invention further comprise the therapeutic dose of the reversibly inactivated acidified plasmin in the range of between about 0.01 mg plasmin/kg body weight and 10 mg plasmin/kg body weight.

In embodiments of the method of the present invention, the reversibly inactivated acidified fibrinolytic composition is administered intravascularly or intrathrombus. In one embodiment of the method of the present invention, the reversibly inactivated acidified plasmin in a low pH-buffered capacity buffer is administered directly into, or proximally to a thrombus by an intravascular catheter device. In still another embodiment of the method of the present invention, the intravascular catheter is directed to a vascular occlusion.

Even though the invention has been described with a certain degree of particularity, it is evident that many alternatives, modifications, and variations will be apparent to those skilled in the art in light of the present disclosure. Accordingly, it is intended that all such alternatives, modifications, and variations that fall within the spirit and the scope of the invention be embraced by the defined claims.

The following examples are presented to describe preferred embodiments and utilities of the present invention, but should not be construed as limiting thereof.

It should be appreciated by those of skill in the art that the techniques disclosed in the examples that follow represent techniques discovered by the inventors to function well in the practice of the invention, and thus can be considered to constitute preferred modes for its practice. Those of skill in the art, in light of the present disclosure, will appreciate that many changes can be made in the specific embodiments disclosed and still obtain like or similar results without departing, again, from the spirit and scope of the present invention.

EXAMPLE 1

Sources of Proteins Investigated

Plasminogen was purified from Cohn Fraction II+III paste by affinity chromatography on Lys-Sepharose as described by Deutsch & Mertz (1970). Thus, 200 g of the paste was resuspended in 2 liter of 0.15M sodium citrate buffer, pH 7.8. The suspension was incubated overnight at 37° C., centrifuged at 14,000 rpm, filtered through fiberglass and mixed with 500 ml of Lys-Sepharose 4B (Pharmacia). Binding of plasminogen was at room temperature for 2 hours. The Lys-Sepharose was then transferred onto a 2-liter glass filter, and washed several times with 0.15M sodium citrate containing 0.3M NaCl until the absorbance at 280 nm dropped below 0.05. Bound plasminogen was eluted with three 200-ml portions of 0.2M $\epsilon$-aminocaproic acid. Eluted plasminogen was precipitated with 0.4 g solid ammonium sulfate/ml of plasminogen solution. The precipitate of crude (80–85% pure) plasminogen was stored at 4° C.

Low-molecular weight urokinase (LMW-urokinase) (Abbokinase-Abbott Laboratories, Chicago Ill.) was further purified by affinity chromatography on benzamidine-Sepharose. The urokinase was then coupled to CNBr-activated Sepharose 4B by mixing 1.3 mg of LMW-urokinase in 50 mM acetate buffer, pH 4.5, and diluting with 5 ml of the coupling buffer, 0.1M sodium bicarbonate, pH 8.0.

This solution was immediately combined with 5 ml of CNBr-activated Sepharose previously swollen and washed in 0.1M HCl. The coupling occurred for 4 hours on ice with shaking. The excess of the CNBr active group was blocked with 0.1M Tris, pH 8.0. Each batch of urokinase-Sepharose was used 5 times and stored in 50% glycerol in water at 4° C. between the cycles. Tissue plasminogen activator (ACTIVASE™) was from Genentech. Plasminogen-free fibrinogen and $\alpha$-thrombin (3793 U/ml) were from Enzyme Research, Inc. $\alpha_2$-Antiplasmin was obtained from Athens Research Technologies. Commercially available plasmin was from Haemotologic Technologies, Inc. Chromogenic plasmin substrate S2251 was from Chromogenix. $^{125}$I-Labeled human fibrinogen (150–250□Ci/mg) was from Amersham Pharmacia Biotech. SDS-polyacrylamide gel electrophoresis was performed in the Pharmacia Phast System apparatus using pre-made 8–25% gradient gels and SDS-buffer strips.

EXAMPLE 2

Purification of Active Plasmin (i) Activation of Plasminogen to Plasmin Using Urokinase-Sepharose Plasminogen was cleaved to plasmin yielding plasmin without contamination of the final preparation by using an immobilized plasminogen activator. Urokinase cleaves plasminogen directly. Plasminogen activation by urokinase does not depend on the presence of fibrin as in the case of tPA, and urokinase is a human protein. These factors, and its relative low cost, make urokinase the preferred activator, although this does not preclude the use of tPA, streptokinase or any other cleavage means yielding an active plasmin capable of fibrin degradation. The ammonium sulfate precipitate of crude plasminogen was centrifuged at 14,000 rpm and resuspended in a minimal volume using 40 mM Tris, containing 10 mM lysine, 80 mM NaCl at pH 9.0 to achieve the final protein concentration of 10–15 mg/ml. The plasminogen solution was dialyzed overnight against the same buffer to remove ammonium sulfate. The dialyzed plasminogen solution (10–20 ml) was diluted with an equal volume of 100% glycerol and combined with 5 ml of urokinase-Sepharose. The use of 50% glycerol reduces autodegradation of plasmin formed during activation. Plasmin is stable in 50% glycerol and can be stored in this solution at –20° C. for an extended period.

The plasminogen activation occurred at room temperature for between 2 hours and 24 hours depending on the freshness of the urokinase-Sepharose. With a fresh batch of urokinase-Sepharose, activation could be completed in 2 hours. It deteriorates, however, and becomes less efficient after several cycles, necessitating the use of SDS-PAGE under reducing conditions to monitor the progress of plasminogen activation. Upon completion of the activation, the plasmin solution was filtered from the urokinase-Sepharose with a glass filter, and immediately applied to benzamidine-Sepharose.

(ii) Capturing of Plasmin on Benzamidine-Sepharose

Since the plasmin is a serine protease with trypsin-like specificity, benzamidine-Sepharose is an affinity absorbent that allowed capture of the active plasmin. A plasminogen solution in 50% glycerol was applied to the 50 ml benzamidine-Sepharose column equilibrated with 0.05M Tris, pH 8.0, containing 0.5M NaCl with a flow rate of 3 ml/min. The column was run at 3 ml/min at 3–7° C. The front portion of the non-bound peak contained high-molecular weight impurities. The rest of the non-bound peak is represented by residual non-activated plasminogen and by inactive autodegradation products of plasmin.

(iii) Elution of the Bound Plasmin with Low-pH Buffer

To protect plasmin from inactivation at neutral pH conditions, acidic elution conditions were selected. The plasmin bound to benzamidine-Sepharose was eluted with 0.2M glycine buffer, pH 3.0 containing 0.5M NaCl. The bound peak was typically divided into three pools, two front peaks, B1 and B2, and the bulk of the eluted material as B3.

Non-reducing gel analysis showed that all three pools contained highly pure (>95%) plasmin. The gel analysis, however, in addition to the heavy and light chains of plasmin, revealed some low molecular weight bands in a range of 10–15 kDa as a result of partial internal cleavage degradation of the plasmin.

The front portion of peak B1 typically contained most of the low molecular weight impurities. The B2 and B3 pools were less degraded. The front portion of the bound peak had very little of the plasmin activity and was usually discarded. The loss of activity in this material may be due to autodegradation during chromatography, because there is no glycerol present in the eluted material, and the pH of the front portion is intermediate between the pH of the equilibrating and eluting buffers, typically in a range of pH 6–6.5. The eluted plasmin, substantially free of plasminogen activators, was collected in tubes containing 2M glycine buffer, pH 3.0 (10% of the collected volume).

(iv) Formulation of Eluted Material in Acidified Water (pH 3.7)

Eluted plasmin was dialyzed against water that had been acidified to about pH 3.7 with glacial acetic acid, or against water containing 0.15M NaCl also acidified to about pH 3.7 with glacial acetic acid.

Any acid providing a pharmaceutically acceptable acidified carrier having a low buffering capacity buffer and having a pH between about 2.5 to about 4.0 can be used. For example, also contemplated within the scope of this invention is the use of other acids and amino acids such as, but not limited to, inorganic acids, carboxylic acids, aliphatic acids and amino acids including, but not limited to, formic acid, acetic acid, citric acid, lactic acid, malic acid, tartaric acid, benzoic acid, serine, threonine, valine, glycine, glutamine, isoleucine, $\beta$-alanine and derivatives thereof, either singly or any combination thereof, that will maintain the pH in the pharmaceutically acceptable carrier of about 2.5 to about 4.0.

Plasmin is extremely stable in acidified water and can be effectively used in this form for in vitro and in vivo studies. Plasmin specific activity was measured using an adapted caseinolytic assay as described by Robbins & Summaria (1970). One ml of 4% casein solution in acidified water and an appropriate volume of 67 mM sodium phosphate buffer, pH 7.4 was added to a test polycarbonate tube. The solutions were vortexed and incubated at 37° C. for 10 minutes. Plasmin samples or buffer (blank) were added to each tube at 15-second intervals, mixed thoroughly and incubated at 37° C. for 30 minutes. The reaction was stopped with the addition of 3 ml of 15% trichloroacetic acid and the precipitate was allowed to form for 15 minutes. The tubes were centrifuged at 3200 rpm for 20 minutes. The supernatants were transferred to cuvettes and the $A_{280}$ of each sample was determined. The specific caseinolytic activity of each sample was determined by the following formula:

$$\frac{3.27 \times [A_{280}(\text{Plasmin Sample}) - A_{280}(\text{Blank})]}{\mu g \text{ Plasmin in Assay}} = \frac{\text{caseinolytic units}}{(CU)/\text{mg protein}}$$

The plasmin concentration was determined spectrophotometrically using the extinction coefficient of 1.7 for 0.1% solution.

EXAMPLE 3 pH-Dependent Stability of Plasmin

Plasmin exhibits a bell-shaped pH dependence of its catalytic activity. As shown in FIG. 1, plasmin has maximum enzyme activity at pH 7.5–8.0, and its activity rapidly decreases at either more alkaline or more acidic pH values. Plasmin is most inactive, and reversibly so, below pH 4.0, due to the protonation of histidine in the catalytic center, as shown by Robbins & Summaria, (1976) and Castellino & Powell (1981).

Plasmin is very unstable at a physiological pH. Both the heavy chain and light chains of plasmin degraded dramatically within hours at room temperature and 4° C. Plasmin was formulated at 1 mg/ml in 0.04M sodium phosphate, pH 7.4, and incubated at 22° C. or 4° C. for 6 hours. During the incubation, the plasmin integrity was analyzed every two hours by reducing SDS-PAGE analysis. Both the heavy chain and light chain degraded rapidly within hours at 22° C. and 4° C. as shown in Table 1.

Plasmin at 1 mg/ml was incubated at 37° C. for 14 days under different acidic conditions. The changes in plasmin heavy chain and light chain were analyzed by reducing SDS-PAGE. Plasmin was formulated at 1 mg/ml in 0.04M sodium phosphate, pH 7.4 and was also incubated at 4° C. for six hours. During the incubation, the activity of the plasmin sample was measured every two hours by chromogenic potency assay. Plasmin potency was quantitatively measured using the MLA 1600C analyzer (Pleasantville, N.Y.). Plasmin hydrolyzed the chromogenic substrate S-2403 (D-pyroglutamyl-L-Phenylalanyl-L-Lysine-p-Nitroaniline hydrochloride or abbreviated as pyro-Glu-Phe-Lys-pNA) to form peptide and the chromophoric group p-nitroaniline (pNA). The rate of color formation was measured kinetically at 405 nm. The amount of substrate hydrolyzed was proportional to the plasmin activity in the sample. A standard curve was generated from the linear regression of the rate of color formation (OD/min) versus the potency of a plasmin standard. The linear equation together with the observed rate for an unknown sample was used to calculate the potency of unknowns. The potency of plasmin was reported in units of mg/ml.

Plasmin integrity was significantly decreased by incubation at a physiological pH, as shown in Table 2.

TABLE 2

The rapid decrease of plasmin activity in neutral pH solution at 4° C.

| | | | Chromogenic Potency | | | |
|---|---|---|---|---|---|---|
| Plasmin | Buffer | pH | Initial | 2 hr | 4 hr | 6 hr |
| 1 mg/ml | PO$_4$, 0.04 M | 7.4 | 100% | 43.3% | 32.6% | 26.4% |

(*The activity of plasmin solution at initial time point was normalized as 100%.)

Figure 2:
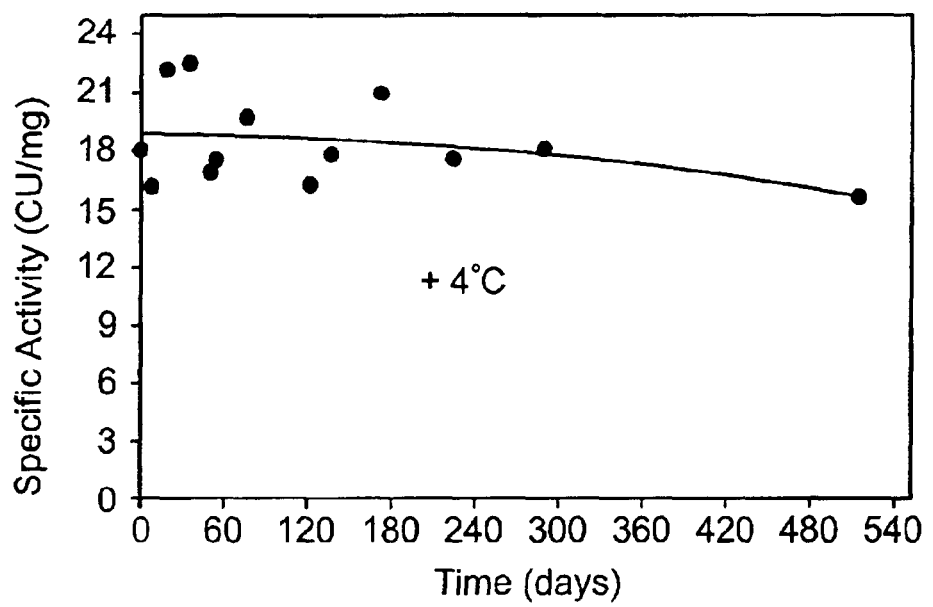
FIG. 2 illustrates plasmin stability in acidified water (pH 3.7) as measured by a caseinolytic assay.
Figure 2:
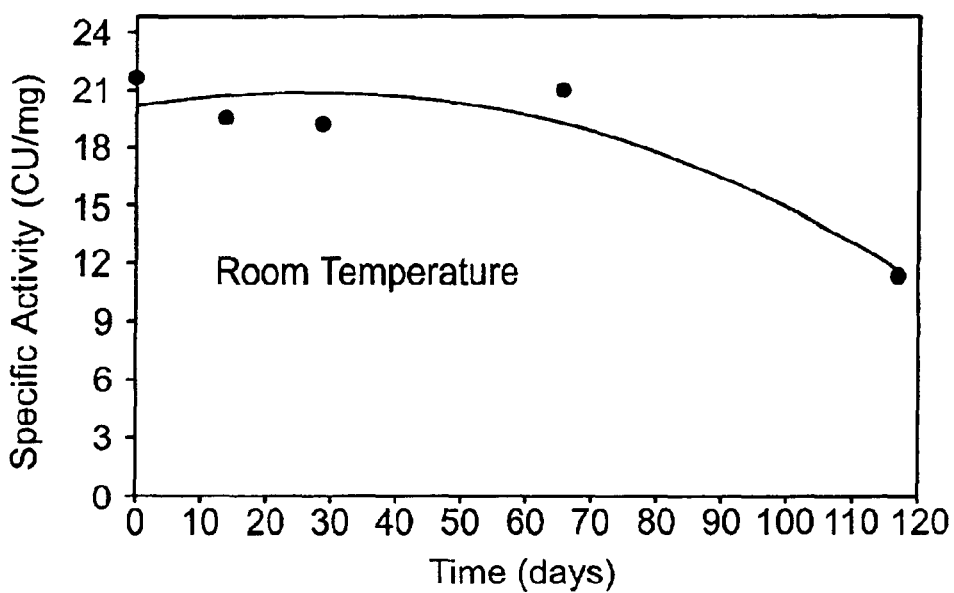

In this neutral pH solution, plasmin activity decreased more than 70% after 6 hours at Plasmin formulated in acidified water at pH 3.7 is stable. It can be kept in this form for months at reduced temperatures without any loss of activity or the appearance of degradation products of a proteolytic or acidic nature. FIG. 2 and the data of Table 3 show the stability of plasmin at 4° C. and at room temperature.

TABLE 1

The rapid degradation of plasmin in neutral pH solution at 22° C. and 4° C.

| | | | | % of intact heavy chain | | | | % of intact light chain | | | |
|---|---|---|---|---|---|---|---|---|---|---|---|
| Plasmin | Buffer | pH | Temp | Initial | 2 hr | 4 hr | 6 hr | Initial | 2 hr | 4 hr | 6 hr |
| 1 mg/ml | 0.04 M PO$_4$ | 7.4 | 22° C. | 100% | 27% | 27% | 29% | 100% | 29% | 26% | 28% |
| 1 mg/ml | 0.04 M PO$_4$ | 7.4 | 4° C. | 100% | 32% | 27% | 25% | 100% | 33% | 25% | 22% |

(The intact heavy chain and light chain of plasmin at initial time point were normalized as 100%.)

TABLE 3

Stability of 1 mg/ml plasmin in the following acidic conditions at 37° C.

| Formulation | Plasmin (mg/ml) | Acidic Condition | pH | % intact heavy chain after 14 days at 37° C. | % intact light chain after 14 days at 37° C. |
|---|---|---|---|---|---|
| 1 | 1 | 5 mM HAC/NaAc | 2.5 | 19% | 62% |
| 2 | 1 | 5 mM HAC/NaAc | 3.0 | 41% | 92% |
| 3 | 1 | 5 mM HAC/NaAc | 3.4 | 48% | 92% |
| 4 | 1 | 5 mM HAC/NaAc | 3.4 | 49% | 96% |
| 5 | 1 | 5 mM HAC/NaAc | 3.4 | 50% | 96% |
| 6 | 1 | 5 mM HAC/NaAc | 3.7 | 13% | 123% |
| 7 | 1 | 5 mM HAC/NaAc | 4.0 | 9.3% | 107% |
| 8 | 1 | 5 mM citric acid/Na citrate | 2.27 | 9.3% | 64% |
| 9 | 1 | 5 mM citric acid/Na citrate | 3.1 | 33% | 68% |
| 10 | 1 | 5 mM citric acid/Na citrate | 3.56 | 46% | 88% |
| 11 | 1 | 5 mM citric acid/Na citrate | 4.0 | 7.4% | 104% |
| 12 | 1 | 5 mM glycine | 2.2 | 7.3% | 104% |
| 13 | 1 | 5 mM glycine | 3.1 | 36% | 70% |
| 14 | 1 | 5 mM glycine | 3.5 | 49% | 85% |
| 15 | 1 | 5 mM glycine | 3.8 | 12% | 85% |
| 16 | 1 | 5 mM glycine | 4.1 | 6% | 81% |
| 17 | 1 | 5 mM serine | 3.4 | 56% | 100% |
| 18 | 1 | 5 mM threonine | 3.4 | 54% | 100% |
| 19 | 1 | 5 mM valine | 3.4 | 52% | 96% |
| 20 | 1 | 5 mM isoleucine | 3.4 | 51% | 100% |
| 21 | 1 | 5 mM β-alanine | 3.7 | 33% | 90% |
| 22 | 1 | 2 mM benzoic acid | 3.5 | 42% | 93% |
| 23 | 1 | 2 mM lactic acid | 3.5 | 45% | 91% |
| 24 | 1 | 2 mM malic acid | 3.5 | 50% | 90% |
| 25 | 1 | 2 mM tartaric acid | 3.5 | 28% | 87% |

(The intact heavy chain and light chain in each formulation before incubation were normalized as 100%; HAc/NaAc = acetic acid/sodium acetate)

Figure 3:
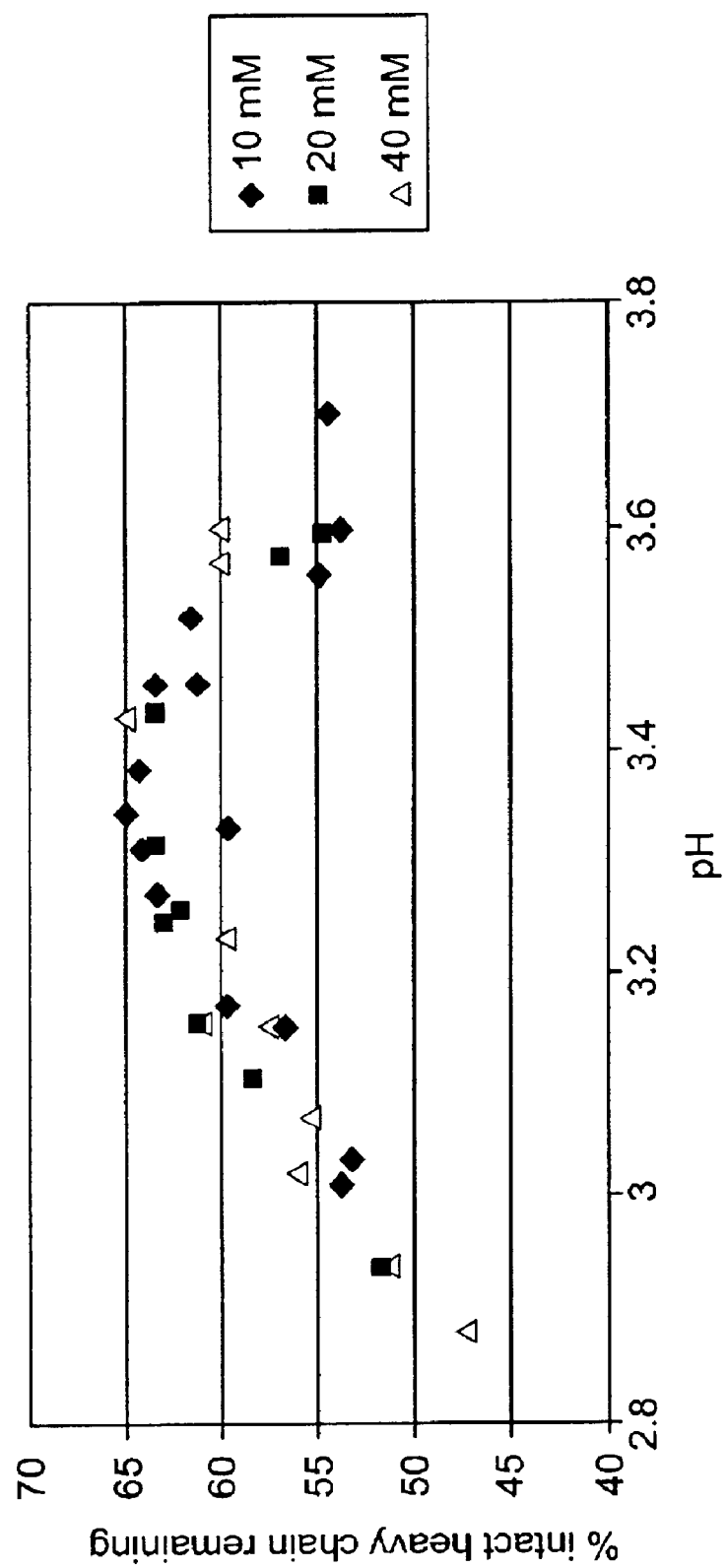
FIG. 3 illustrates a plot of pH versus percent heavy chain relative to total protein in each lane of SDS gels.

At 4° C., plasmin is stable for at least nine months. Even at room temperature, reversibly inactivated acidified plasmin is stable for at least two months. Long-term stability at room temperature is important because it would make this formulation compatible with long regimens of thrombolytic administration. For example, 36 hour administration of thrombolytics such as tissue plasminogen activator or urokinase is common in treatment of peripheral arterial occlusions. Shown in FIG. 3 is a plot of pH versus percent heavy chain relative to total protein in each lane of the SDS gels. The results demonstrate a pH stability optimum of about 3.1–3.5, irrespective of the type of buffer, or buffer concentration.

The ability of reversibly inactivated acidified plasmin to become fully active upon transfer to physiological pH is evidenced by its activity in the caseinolytic assay and also in the $^{125}$I-fibrin-labeled thrombolysis assays. Both of these assays are performed at pH 7.4, and there was complete recovery of plasmin activity during the change of pH and passing through the isoelectric point (pH 5–5.5). The plasmin is formulated in a low-buffering capacity solvent and, when added to a buffered solution such as plasma, it rapidly adopts the neutral or physiological pH instantly and the precipitation that usually accompanies the slow passage through the isoelectric point, does not occur.

EXAMPLE 4

Figure 4:
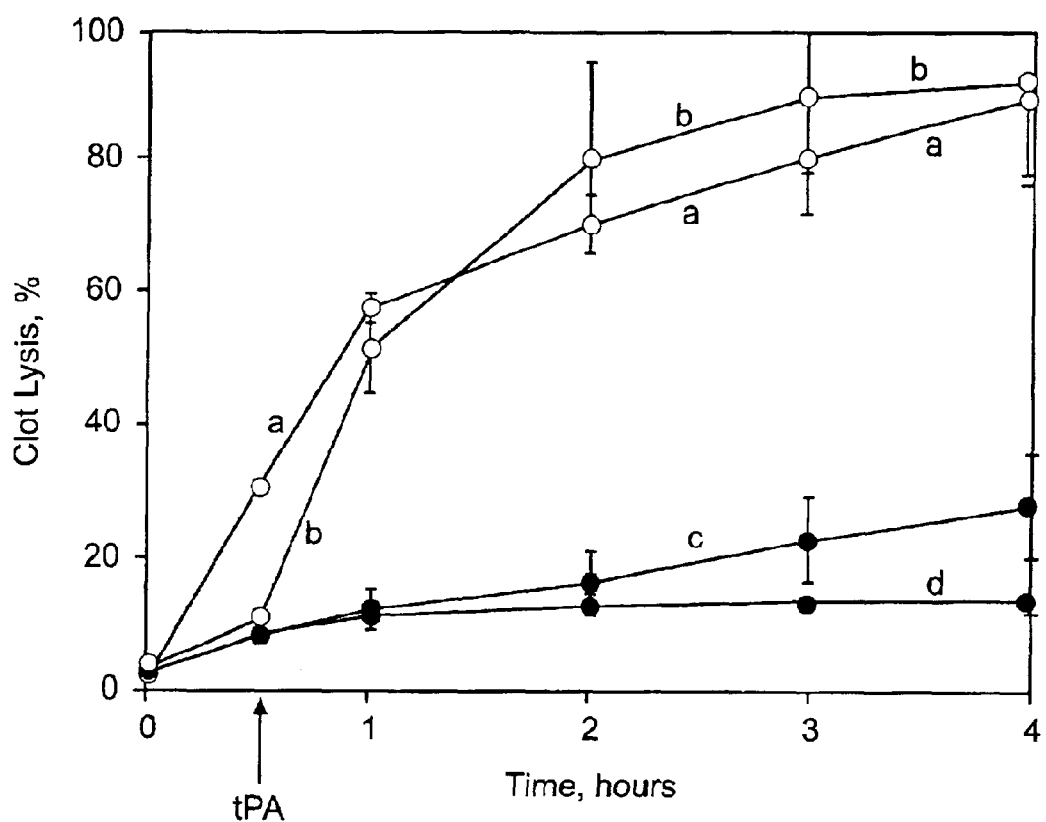
FIG. 4 illustrates the effectiveness of plasmin or tPA plus plasminogen in thrombolysis.

Plasmin has the Same Intrinsic Fibrinolytic Potency as a Plasminogen/Plasminogen Activator Mixture Plasmin has the same intrinsic fibrinolytic potency as a plasminogen/plasminogen activator mixture. Fibrinolytic potency of plasmin was compared with that of a Lys-plasminogen and tPA mixture. These experiments were performed in a defined system consisting of an $^{125}$I-radiolabeled fibrin thrombus submersed in PBS. FIG. 4 shows that, in a buffered environment, thrombolysis achieved with plasmin is almost identical to the Lys-plasminogen plus tPA mixture (curves a and b, respectively). At the same time, no thrombolysis was observed with tPA alone (curve c) or in the absence of any proteins (curve d). The data obtained with tPA alone shows that its activity is dependent on its substrate, plasminogen, to be an effective thrombolytic.

These data indicate that, in the absence of inhibitors and other protein factors present in plasma, there is no difference in the ability to lyse fibrin thrombi between purified plasmin and the combination of tPA and Lys-plasminogen activated with tPA. In order to assess the thrombolytic potency of active plasmin, the $^{125}$I-fibrin-labeled thrombolysis assay was performed with plasma thrombi in a plasma environment.

EXAMPLE 5

Role of Plasmin Inhibitors in Regulating Plasmin Activity $^{125}$I-fibrin labeled thrombolysis assay. The fibrinolytic properties of plasmin were determined in an in vitro system consisting of a radio-labeled plasma thrombus immersed in human citrated plasma as described by Lijnen et al. (1986). Plasma used in all experiments was single donor plasma thawed at 37° C., aliquoted, re-frozen and stored at −80° C. The stock solution of $^{125}$I-labeled fibrinogen was prepared by rehydrating the contents of the vial (approximately 110 µCi/vial) with 1.0 ml of 0.15M sodium citrate and was stored at 4° C.

Ten µl of $^{125}$I-fibrinogen was added to a polycarbonate test tube containing 250 µl of plasma at 37° C. and mixed briefly. Twenty-five µl of a-thrombin, diluted with 0.1M CaCl$_2$ to a final concentration of 10–20 µM, was added to the plasma. The radio-labeled thrombi were allowed to age for five minutes at 37° C. and then washed with PBS. The thrombi were transferred into test tubes containing 2.25 ml plasma or buffer, one thrombus per tube.

A baseline radioactivity sample was measured for each thrombus. Plasmin was added to each tube after the addition of each thrombus. The thrombi were returned to 37° C. for the duration of the experiment. Further samples were taken at indicated time points for measurement of released radioactivity. The extent of thrombolysis was calculated from the ratio between the amount of radioactivity released from the thrombus into the plasma and the total amount of soluble radioactivity in the reaction tube. The release of labeled fibrin degradation products, expressed in percent, was plotted versus time.

In addition to the plasma milieu, some thrombolysis experiments were conducted in a buffer environment or with plasma lacking α$_2$-antiplasmin or α$_2$-macroglobulin activity. α$_2$-antiplasmin-depleted plasma was obtained by passing normal plasma through a Kringles 1–3-Sepharose column as described by Wiman (1980). α$_2$-Macroglobulin-inactivated plasma was obtained by treatment of normal plasma with 0.1M methylamine Barrett et al. (1979) for 2 hours at 37° C. with subsequent dialysis against PBS at 4° C.

Figure 5:
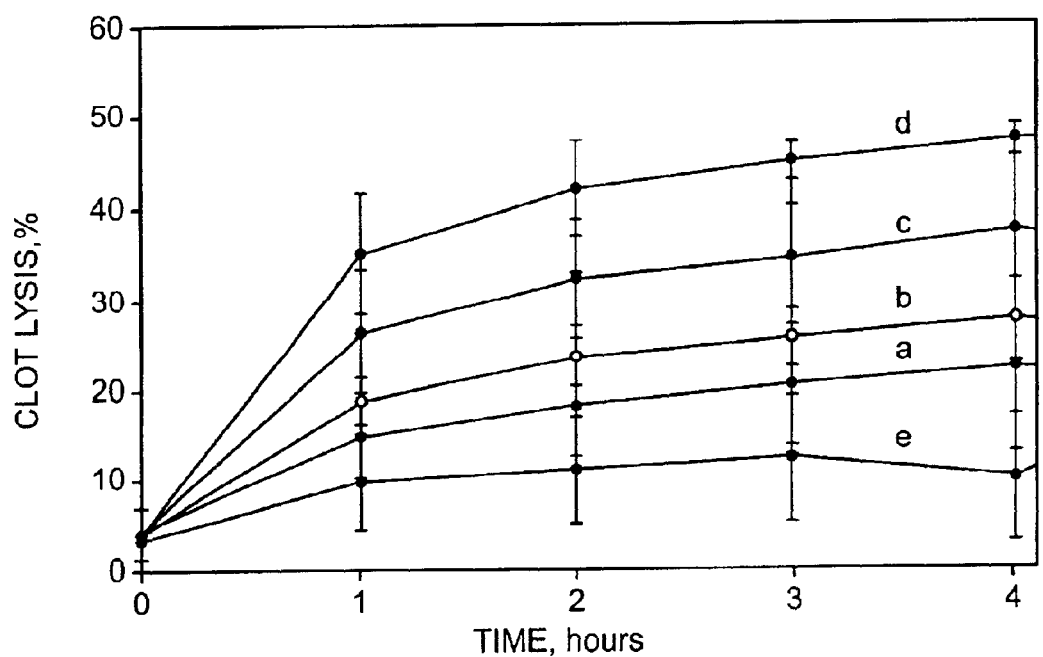
FIG. 5 illustrates thrombolytic potency of active plasmin.
Figure 6:
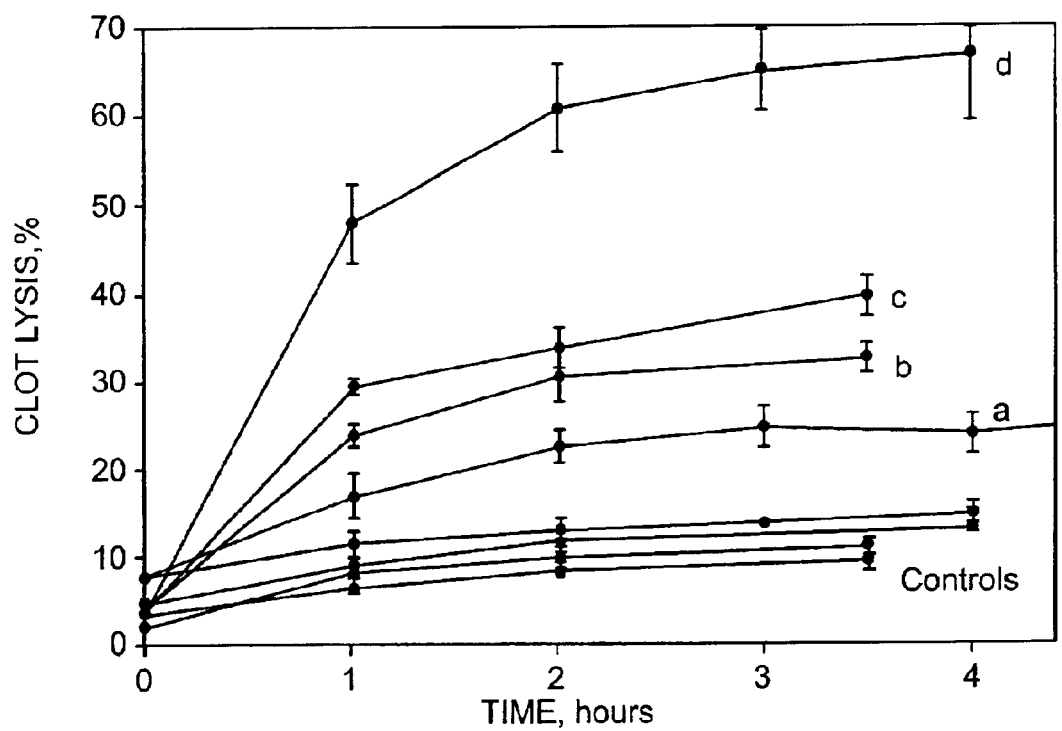
FIG. 6 illustrates the effect of plasma inhibitors on plasmin-induced thrombolysis.

Using the above-described thrombolysis assay, it was shown that plasmin was capable of dissolving plasma thrombi in a dose-dependent manner as shown in FIGS. 5 and 6. Increasing amounts of plasmin were added to 125I fibrin-labeled plasma thrombi and the degree of thrombolysis was assessed by measuring the release of radioactivity: (a) 0.15 mg/ml of plasmin in the reaction tube, (b) 0.30 mg/ml; (c) 0.45 mg/ml; (d) 0.60 mg/ml; (e) control with no plasmin added. The data in FIG. 6 demonstrate that plasmin is also active in a plasma environment and is capable of dissolving plasma thrombi. This phenomenon is dose-dependent. At the same time, unlike with the Lys-plasminogen and tPA mixture, thrombolysis by plasmin alone does not progress to completion in a plasma environment; thrombolysis tends to cease after 2 hours. While not wishing to be bound by any one theory, this phenomenon can be explained by the presence of various protease inhibitors in a plasma environment and, especially by rapid inhibition of non-thrombus-bound plasmin by α$_2$-antiplasmin.

To assess the role of plasma inhibitors in plasmin-catalyzed thrombus lysis, a series of thrombolysis experiments was performed with normal plasma and plasma samples lacking α$_2$-antiplasmin, α$_2$-macroglobulin or all the inhibitors, or PBS.

As seen from FIG. 6, plasmin-induced fibrinolysis was enhanced by deletion of either α$_2$-antiplasmin or α$_2$-macroglobulin in the plasma surrounding the thrombus, and even more so by the deletion of all inhibitors. These results confirm that thrombolysis by plasmin is under very strict physiologic control by the endogenous plasma plasmin inhibitors, thus providing a basis for safer thrombolytic therapy.

In contrast to plasminogen activator-induced thrombolysis, thrombolysis with plasmin can be controlled by these inhibitors. Plasminogen activator-induced thrombolysis utilizes the internal source of plasminogen present in plasma that, from the practical point of view, is unlimited in a human body. On the other hand, plasmin-induced thrombolysis entirely depends on the external source of the plasmin. Cessation of plasmin administration to the patient should result in rapid cessation of thrombolysis and provides a basis for safer thrombolytic therapy.

EXAMPLE 6

Comparison of Reversibly Inactivated Acidified Plasmin and tPA in an in vitro Model of Peripheral Arterial Occlusion (PAO)

Aged, retracted clots are deficient in plasminogen, the substrate required by all plasminogen activators for effective clot lysis. Robbie et al. Thrombosis and Haemostasis, 1996, 75(1), 127–33. Aged clots are significantly less susceptible to lysis by plasminogen activators.

Aged clots differ from clots causing myocardial infarction or stroke both mechanically and in their protein composition. They are typically found in the peripheral arteries and can grow to a significant size. The average size of a peripheral clot found in the native arteries is 14.8±11 cm as described in Ouriel et al. Current thrombolytics represented exclusively by plasminogen activators are almost ineffective in lysis of these types of clots. Typically, a patient with PAO is treated for more than 24 hours with urokinase and even after this prolonged time, the complete patency of the vessel is not achieved. The situation may be exacerbated when the thrombolytics are delivered via catheter into the interior of the clot, further preventing the access of the plasminogen substrate required for their efficacy.

Another approach to the lysis of retracted clots is the direct delivery of active plasmin via a catheter, into the interior of the clot. Delivery of reversibly inactivated acidified plasmin directly into retracted clots circumvents the inherent plasminogen deficiency of these clots and provides predictable, rapid and effective clot thrombolysis irrespective of plasminogen content. Moreover, the abundant presence of the natural plasmin inhibitor, α$_2$-antiplasmin, in plasma serves to instantaneously inactivate any plasmin which escapes from the vicinity of the clot, thereby preventing distal fibrinolysis and consequent bleeding episodes.

To compare the efficacy of plasmin and tPA toward the lysis of long retracted clots, we have developed an in vitro model that mimics parameters of the clots formed in patients with PAO.

In Vitro PAO Model. Fresh whole human blood was collected into 30×0.95 cm glass tubes and allowed to clot spontaneously without additives. Tubes were incubated for 20 hours at 37° C. to allow full retraction. Retracted clots were separated from serum using USA Standard testing sieves D16 with 14 mesh and their weights were determined. Blood clots were transferred into smaller diameter glass tubes that resembled the average size clots in leg arteries (0.6×12 cm). A multi-side port pulse-spray catheter (French size 5 with the 11 cm spraying tip, Cook, Inc.) was inserted into the clot and a thrombolytic reversibly inactivated acidified plasmin composition according to the present invention, or tpA) at 1 mg/ml was delivered in 1-ml increments separated by 1 hour time intervals. The number of injections corresponds to the dose of thrombolytic. The extent of clot lysis was measured by the weight of a residual clot and expressed as a percent of clot weight reduction. This model is called a PAO model. It mimics the dimensions of the thrombi found in PAO patients, although venous blood was used for clot formation. Both tPA and the reversibly inactivated acidified plasmin composition according to the present invention were tested in this model and the results are presented below.

Plasmin is as effective as tPA for lysis of fresh clots, unlike when tPA and plasmin are used for lysis of retracted clots aged for 20 hours to allow complete cross-linking by Factor XIII. tPA is unable to lyse such clots. Clot weight reduction obtained with tPA-treated clots is similar to the control, even when the dose is raised up to 5 mg per clot.

Plasmin, on the other hand, is effective toward fully retracted and cross-linked clots. There is a dose-dependence of the lytic effect of plasmin and after five injections (or 5 mg plasmin in total) the clots are almost completely lysed. In a similar series of experiments, the same inability to dissolve retracted and cross-linked human thrombi was observed with urokinase. Locally delivered plasmin therefore is a more effective thrombolytic agent than tPA and other plasminogen activators.

These in vitro data show that tPA requires the presence of its substrate, plasminogen, in the clot to initiate and maintain clot lysis. Therefore, while plasmin is as effective as tPA for lysing fresh or plasminogen-rich clots, plasmin is more effective that tPA, and other plasminogen activators, for lysing of long retracted plasminogen-poor clots. Moreover, the data presented in this example demonstrates that plasmin is effective in its reversibly inactivated acidified form when it is injected directly inside the clot.

The clots in the glass tubes are also a model wherein a thrombus or fibrin plug forms in catheters placed in a human or animal and the catheter is occluded.

EXAMPLE 7

Rabbit Jugular Vein Thrombosis Model

The in vivo efficacy and safety of locally administered active plasmin was determined by the rabbit jugular vein thrombosis model of Collen et al., (1983). The model, in brief was as follows: Rabbits (2–3 kg) are sedated with ketamine/xylazine and a 22G venous catheter was placed in the ear vein for administration of a dilute solution of pentobarbital (5–10 mg/kg/hr). The neck was shaved and an arterial catheter was placed in the carotid artery for pressure measurements and blood sampling. A tracheotomy was performed for placement of a tracheal tube to facilitate breathing. The jugular vein was carefully isolated with blunt dissection up to and including the facial vein. A 24G catheter was placed in the facial vein and the jugular vein clamped both distal and proximal to the isolated facial vein. The isolated vein segment was washed several times with saline and completely drained of blood. The isolated segment was washed several times with a thrombin solution (500 U/ml). Following the last wash, 0.5 ml of arterial blood sample was drawn from the arterial catheter and mixed quickly with 50 μl of $^{125}$I-labelled fibrinogen (approximately 1 μCi). The mixture was rapidly infused into the isolated vein segment via the facial vein until the vein segment was fully distended. The thrombus was mixed by massaging the vein with forceps and a piece of Saran Wrap placed over the exposed jugular vein to prevent drying. Heparin (100 IU/kg) was administered to prevent the deposition of cold fibrinogen on thrombus. The thrombus was allowed to age for 30 minutes and clips were removed.

The stability of the thrombus is monitored over a 30-minute equilibration period. Dissolution of the labeled thrombus (% lysis) was monitored continuously with a G1LE gamma counter probe placed directly over the thrombus.

EXAMPLE 8

Restoration of Venous Flow

To provide a physiologic readout of thrombus dissolution, blood flow restoration was used as another index of thrombolysis in a separate series of experiments. In these experiments, an appropriately sized flow probe was placed distal to the occlusive thrombus (not radiolabeled) connected to a Transonic Flowmeter and venous blood flow measurements were taken every minute.

Figure 7:
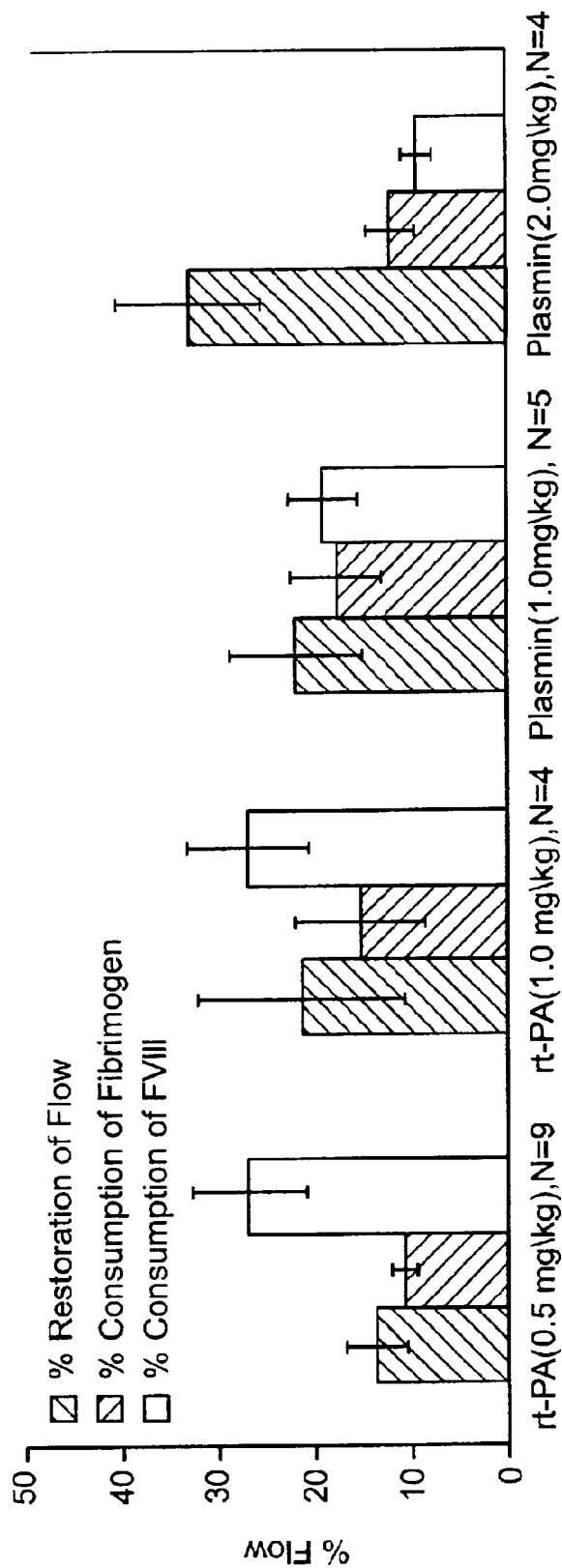
FIG. 7 compares local administration of tPA or Lys-plasmin on blood flow restoration, and FVIII and fibrinogen consumption, at 60 minutes.
Figure 8:
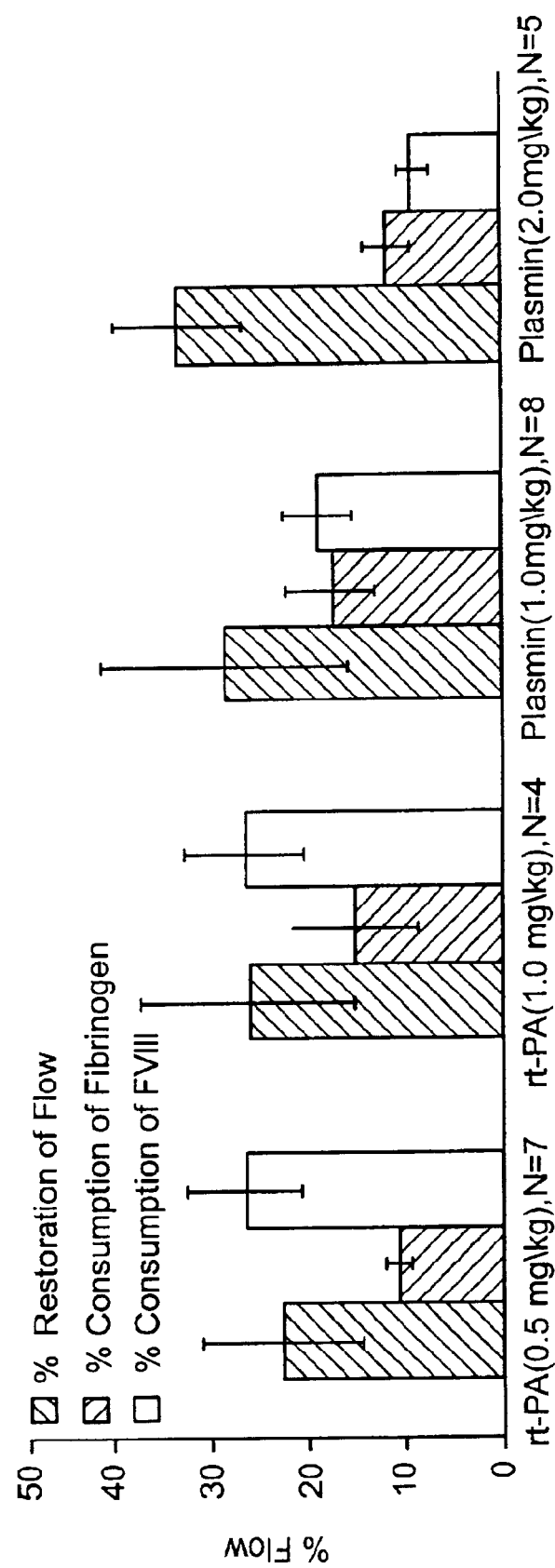
FIG. 8 compares local administration of tPA or Lys-plasmin on blood flow restoration at 90 minutes, and FVIII and fibrinogen consumption at 60 minutes.

Baseline blood flow before thrombus formation was 12–18 ml/min and data is represented as % of baseline. The percent restoration of venous blood flow and the consumption of Factor VIII and fibrinogen are shown at 60 minutes in FIG. 7, and at 90 minutes in FIG. 8. At doses of 0.5 mg/kg and 1.0 mg/kg, tPA induced 16±4% and 21±10% restoration of baseline blood flow at 60 minutes, respectively. Plasmin at 1.0 mg/kg and 2.0 mg/kg induced 20±1% and 33±1% restoration of baseline blood flow, respectively. At 90 minutes, tpA infusion resulted in 18±3% and 26±11% restoration of blood flow, respectively and plasmin had resulted in 25±5% and 34±6% restoration of flow, respectively.

EXAMPLE 9

Cuticle Bleeding Times (CBT)

Figure 9:
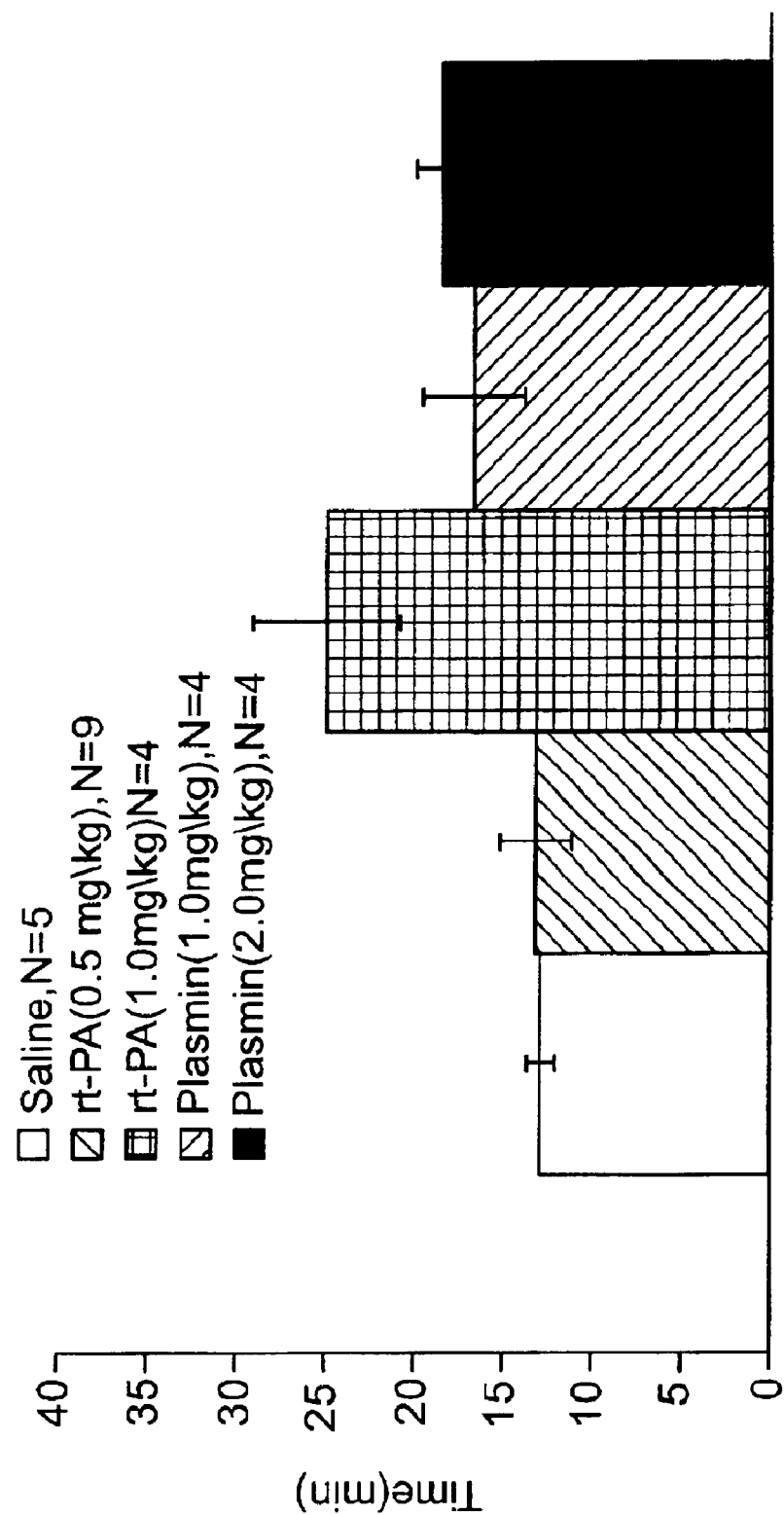
FIG. 9 illustrates the effect of local administration of tPA versus plasmin on cuticle bleed times.

Cuticle bleeding times at 60 minutes are shown in FIG. 9. Saline treatment resulted in bleeding times of 13±1 minutes. tPA at doses of 0.5 mg/kg and 1.0 mg/kg resulted in bleeding times of 13±2 minutes and 25±4 minutes, respectively, whereas plasmin, at doses of 1.0 mg/kg and 2.0 mg/kg resulted in bleeding times of 17±3 and 19±1 minutes, respectively. tPA shows a prolonged CBT compared to when reversibly inactivated acidified plasmin is used, demonstrating that systemic fibrinolysis by tPA activation of endogenous plasminogen is more extensive than if plasmin is administered and rapidly inhibited by serum factors.

EXAMPLE 10

Rabbit Fibrinolytic Hemorrhage Model

The greater safety of plasmin, relative to the plasminogen activator tPA, was demonstrated in an established rabbit model of fibrinolytic bleeding that represents a valid indication of fibrinolytic hemorrhage, as described in Marder et al., (1992).

Thrombolytically equivalent doses (10 ml volumes) of plasmin and tpA were compared in ear-puncture model for their relative effects on the occurrence and duration of re-bleeding, and on selected plasma coagulation and fibrinolytic parameters. Two different doses of plasmin (2.0 or 4.0 mg/kg) or tPA (1.0 or 2.0 mg/kg) were infused over 60-minute periods into rabbits through a catheter inserted into the external jugular vein. Ear punctures (approximately six per ear) with a scalpel blade prior to, during, and after infusion of each fibrinolytic agent were observed for both bleeding time and for re-bleeding. Primary bleeding times were performed at minus 30, minus 10, 0, 10, 30, 60, 70, 90, 120 and 180 minutes relative to the start of each infusion. Citrated blood samples (5 ml) were obtained before, during, and for up to two hours after infusion of each fibrinolytic agent; these blood samples were assayed for fibrinogen, Factor VIII, and $\alpha_2$-antiplasmin. Each experimental group consisted of five rabbits.

The primary bleeding times tended to be longer for the tPA groups at each time point after initiation of infusion until the 90-minute point (Table 4).

TABLE 4

Primary bleeding times.

| Experimental Group | Mean Bleeding Time for Group (Minutes) at Different Times (Minutes) Relative to the Start of Infusion | | | | | | | | | |
|---|---|---|---|---|---|---|---|---|---|---|
| | −30 | −10 | 0 | 10 | 30 | 60 | 70 | 90 | 120 | 180 |
| tPA (1.0 mg/kg) | 2.2 | 1.7 | 1.4 | 3.3 | 2.8 | 2.5 | 1.6 | 1.6 | 1.2 | 2.4 |
| tPA (2.0 mg/kg) | 1.7 | 1.9 | 1.6 | 1.6 | 2.7* | 3.9 | 3.0* | 2.3 | 1.7 | 1.0 |
| Plasmin (2.0 mg/kg) | 1.6 | 1.7 | 1.8 | 2.0 | 1.9 | 2.5 | 1.8 | 2.2 | 2.0 | 1.7 |
| Plasmin (4.0 mg/kg) | 1.5 | 1.5 | 1.4 | 2.3 | 1.1* | 2.8 | 1.4* | 0.9 | 1.4 | 1.5 |

*Statistically greater than the corresponding mean values observed with the indicated plasmin groups ($p < 0.05$).

This effect was statistically significant ($p<0.05$) in the comparison of the high-dose groups of tPA and plasmin at the 30-minute and 70-minute experimental times.

Table 5 shows the observed occurrence of re-bleeding in each of the four experimental groups.

TABLE 5

Occurrence of Re-bleeding in Each Experimental Group

| Experimental Group | Number of Animals Exhibiting Re-Bleeding |
|---|---|
| tPA (1.0 mg/kg) | 5 out of 5 |
| tPA (2.0 mg/kg) | 4 out of 5 |
| Plasmin (2.0 mg/kg) | 0 out of 5 |
| Plasmin (4.0 mg/kg) | 0 out of 5 |

TABLE 5-continued

Occurrence of Re-bleeding in Each Experimental Group

| Experimental Group | Number of Animals Exhibiting Re-Bleeding |
|---|---|
| tPA combined groups (n = 10) | 9 out of 10 |
| Plasmin combined | 0 out of 10 |

The results distinguish the hemorrhagic activity of the plasminogen activator, tPA, from that of plasmin. None of the plasmin-treated animals exhibited re-bleeding, unlike nine out of ten of the tPA-treated animals.

Table 6A summarizes the mean re-bleeding times at active sites and at all sites of re-bleeding for the 1.0 mg/kg tPA dosage group. Table 6B summarizes the corresponding data for the 2.0 mg/kg dosage group.

TABLE 6A

Mean Re-bleeding Times in Rabbits Receiving tPA at 1.0 mg/kg

| | Time Relative to Start of Infusion (Minutes) | | | | | | | | | |
|---|---|---|---|---|---|---|---|---|---|---|
| | −30 | −10 | 0 | 10 | 30 | 60 | 70 | 90 | 120 | 180 |
| Percentage of sites that re-bled | 60 | 60 | 80 | 100 | 80 | 20 | 20 | 0 | 0 | 0 |
| Mean re-bleeding time (minutes) of active sites | 2.0 | 4.0 | 31.3 | 20.7 | 9.0 | 1.5 | 1.0 | — | — | — |
| Mean re-bleeding time (minutes) of all sites | 1.2 | 2.4 | 25.0 | 20.7 | 7.2 | 0.3 | 0.2 | — | — | — |

TABLE 6B

Mean Re-bleeding Times in Rabbits Receiving tPA at 2.0 mg/kg

| | Time Relative to Start of Infusion (Minutes) | | | | | | | | | |
|---|---|---|---|---|---|---|---|---|---|---|
| | −30 | −10 | 0 | 10 | 30 | 60 | 70 | 90 | 120 | 180 |
| Percentage of sites that re-bled | 40 | 80 | 60 | 80 | 60 | 40 | 0 | 0 | 0 | 0 |
| Mean re-bleeding time (minutes) of active sites | 32 | 23 | 44.7 | 68.4 | 48.7 | 2.5 | — | — | — | — |
| Mean re-bleeding time (minutes) of all sites | 12.8 | 18.4 | 26.8 | 54.7 | 7.2 | 29.2 | — | — | — | — |

Re-bleeding at active sites showed a distinction between the two dosage groups for tPA, with longer duration of re-bleeding at the 2.0 mg/kg dose relative to the 1.0 mg/kg dose of tPA. The results from blood chemistry measurements are summarized in Tables 7–9.

Table 7 presents the levels of fibrinogen measured at the experimental times. The mean fibrinogen levels following tPA infusion fell more rapidly and to a lower nadir than following the plasmin infusions.

TABLE 7

Mean Fibrinogen Levels (mg/dl) in Experimental Groups at Different Times (Minutes) Relative to Start of 60-Minute Infusion

| | Time Relative to Start of Infusion (Minutes) | | | | | | | |
|---|---|---|---|---|---|---|---|---|
| Experimental Group | −30 | 0 | 10 | 60 | 70 | 90 | 120 | 180 |
| tPA (1.0 mg/kg) | 221 | 205 | 202 | 93 | 145 | 126 | 194 | 205 |
| tPA (2.0 mg/kg) | 260 | 233 | 151 | 118 | 196 | 190 | 214 | 160 |
| Plasmin (2.0 mg/kg) | 208 | 231 | 214 | 149 | 167 | 134 | 183 | 145 |
| Plasmin (4.0 mg/kg) | 297 | 293 | 256 | 222 | 146 | 184 | 159 | 140 |

The mean values for Factor VIII (Table 8) were lower at most of the experimental times for the tPA-infused animals relative to the plasmin-infused animals, with statistical significance being reached at the 60-minute experimental time for each tPA group versus each plasmin group.

TABLE 8

Mean Factor VIII Levels (Percent of Initial) in Experimental Groups at Different Times (Minutes) Relative to Start of 60-Minute Infusion

| | Time Relative to Start of Infusion (Minutes) | | | | | | | |
|---|---|---|---|---|---|---|---|---|
| Experimental Groups | −30 | 0 | 10 | 60 | 70 | 90 | 120 | 180 |
| tPA (1.0 mg/kg) | (100) | 87 | 84 | 23* | 58 | 77 | 57 | 64 |
| tPA (2.0 mg/kg) | (100) | 85 | 56 | 29* | 41 | 36 | 46 | 44 |
| Plasmin (2.0 mg/kg) | (100) | 108 | 87 | 77 | 62 | 56 | 72 | 78 |
| Plasmin (4.0 mg/kg) | (100) | 85 | 65 | 58 | 58 | 61 | 47 | 50 |

*Statistically lower than the corresponding mean values for either of the plasmin groups at 60 minutes (p < 0.05).

Recovery of Factor VIII in animals receiving tPA was to approximately the same concentration (50–60% of initial values) as with animals receiving plasmin. Comparison of the two doses of tPA shows a more rapid decrease in Factor VIII with the higher dose and a more dramatic rebound increase in Factor VIII with the lower dose.

The mean values for $\alpha_2$-antiplasmin as shown in Table 9 were lower at most of the experimental times for the tPA-infused animals relative to the plasmin-infused animals.

TABLE 9

Mean $\alpha_2$-Antiplasmin Levels (Percent of Initial) in Experimental Groups at Different Times (Minutes) Relative to Start of 60-Minute Infusion

| | Time Relative to Start of Infusion (Minutes) | | | | | | | |
|---|---|---|---|---|---|---|---|---|
| Experimental Group | −30 | 0 | 10 | 60 | 70 | 90 | 120 | 180 |
| tPA (1.0 mg/kg) | (100) | 100 | 39* | 4* | 34 | 37 | 51 | 43 |
| tPA (2.0 mg/kg) | (100) | 81 | 12* | 0* | 9** | 15** | 15 | 27 |
| Plasmin (2.0 mg/kg) | (100) | 104 | 93 | 55 | 55 | 56 | 45 | 79 |
| Plasmin (4.0 mg/kg) | (100) | 102 | 89 | 45 | 20 | 49 | 24 | 24 |

*Statistically lower than the corresponding mean values for either of the plasmin groups at these experimental times (p < 0.05).
**Statistically lower than the mean values for the low-dose plasmin groups at these experimental times (p < 0.05).

Statistical significance was reached at the 10-minute and 60-minute experimental times between each of the tPA groups and either of the plasmin groups and at the 70-minute and 90-minute experimental times between the high-dose tPA groups and the corresponding low-dose plasmin groups.

EXAMPLE 11

Fibrinolysis by Mini-plasmin

Mini-plasmin is a truncated version of plasmin lacking the first four kringle domains. It can be produced from mini-plasminogen that is generated by limited proteolysis of plasminogen with elastase. Mini-plasmin will be more effective for clot lysis than fill-sized plasmin since: (a) mini-plasmin is smaller than plasmin (38 kDa vs 84 kDa) and will more easily diffuse inside the clot; and (b) mini-plasmin lacks the $\alpha_2$-antiplasmin binding site of kringle 1, and therefore will be resistant to inhibition by $\alpha_2$-antiplasmin cross-linked to the clot. $\alpha_2$-Antiplasmin is often responsible for resistance of aged clots to thrombolytic therapy. Mini-plasminogen was purified as described in Sottrup-Jensen et al. (1975). Mini-plasminogen conversion into mini-plasmin, its purification and formulation were accomplished using exactly the protocol as described for plasmin of the Example 2.

The thrombolytic potency of mini-plasmin was compared with that of plasmin at equimolar concentrations using the in vitro PAO model described in Example 6. Clots were aged for 20 hours and two 1-ml doses of plasmin (1 mg/ml) or mini-plasmin (0.45 mg/ml) were delivered to the clot via a catheter. Between injections, clots were incubated at 37° C. for 1 hour. The extent of thrombolysis was measured by clot weight reduction. Clots infused with saline were used as control. Clot dimensions –0.6×12 cm.

Figure 10:
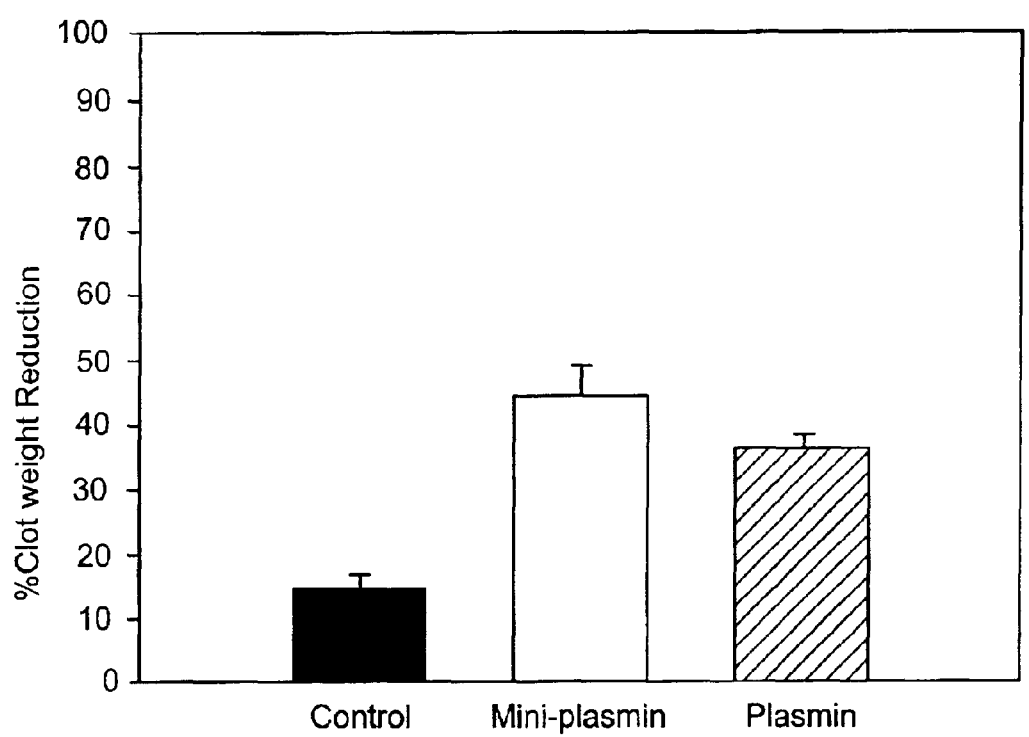
FIG. 10 illustrates lysis of retracted blood clots with equimolar amount of reversibly inactivated acidified plasmin or mini-plasmin.

As shown in FIG. 10, mini-plasmin causes greater clot lysis than plasmin when used in the equimolar amounts. The clot weight reduction after two 1-ml injections of mini-plasmin at 0.45 mg/ml was 44.3±4.4%. whereas two 1-ml injections of plasmin at 1 mg/ml resulted in 36±1.7% clot weight reduction. Mini-plasmin can be an even more effective thrombolytic agent than plasmin when delivered through the catheter directly to or inside the clot.

EXAMPLE 12

Efficacy of Localized Catheter Plasmin Administration of Plasmin

The in vivo efficacy of plasmin (1–2 mg/kg) administered locally via a catheter was compared with that of tPA (0.5 and 1.0 mg/kg) in the rabbit jugular vein thrombosis model. Two approaches were used to assess thrombolysis: 1) real-time measurements of percent lysis with a radiolabeled thrombus; and 2) restoration of baseline blood flow via the application of a flow probe and flow meter. The rate of thrombolysis was monitored and quantified over 90 minutes, as described in Example 6. Concomitantly, the consumption of Factor VIII and fibrinogen, as well as cuticle bleeding time (CBT), were measured as indicators of the systemic lytic state. For these local administration studies, a catheter (PE 50) was advanced via the marginal ear vein, to within 1 cm of the obstructive thrombus. Two doses of tPA; 0.5 and 1.0 mg/kg and two doses of plasmin; 1.0 mg/kg and 2 mg/kg were used. These doses were contained in 10.0 ml total volume infused over 30 minutes. The percent lysis at 60 and 90 minutes with the radiolabeled thrombus was measured and, in another separate series of experiments with unlabelled thrombi, percent restoration of flow was measured at similar time points. Arterial blood samples (4 ml) obtained at 0 minutes and 60 minutes were used for determination of fibrinogen and Factor VIII levels. Factor VIII levels and fibrinogen concentrations were determined using a MLA Electra 800 Coagulation Timer and the Fibrinogen Assay Set. Factor VIII levels were determined by the COATEST VIII C4 assay using human Factor VII to generate a standard curve. Cuticle bleeding times at 0 minutes and 60 minutes were determined by clipping the rabbit's nail, at the apex, with a dog nail trimmer. The blood was dabbed, without touching the nail, with a filter paper every two minutes until a thrombus formed and the filter paper did not wick blood away. Results are represented as Mean±SEM, and to evaluate significant differences between groups a one-way ANOVA followed by Bonferroni's procedure for multiple-comparison testing was used. P<0.05 was considered significant.

Plasmin or tPA (total volume 10 ml) was infused over 30 minutes via a catheter placed 1 cm proximal to the thrombus. An equal volume of saline served as a control. Plasmin doses of 1.0–2.0 mg/kg were compared to a 0.5 mg/kg dose of tPA. A one-way ANOVA followed by Dunn's method for multiple comparison testing was used for statistical evaluation, (* p<0.05 compared to tPA at 0.5 mg/kg, or # vs tPA at 1.0 mg/kg).

When compared with tPA (0.5 –1.0 mg/kg), plasmin (1.0–2.0 mg/kg) infused locally induced comparable or significantly better thrombolysis, with similar or less consumption of Factor VIII and fibrinogen and CBT. Risk/benefit evaluation of plasmin treatment revealed that twice the dose of plasmin (on a weight basis) induced similar bleeding side effects as did tPA. Thus, plasmin can be effectively and safely used as a thrombolytic agent during catheter-assisted local thrombolysis. Plasmin has comparable or superior lytic activity when compared to tPA, and the safety profile appeared similar in this animal model of local thrombolytic delivery.

The extent of thrombolysis was calculated from the ratio between the amount of radioactivity released from the thrombus into the plasma and the total amount of radioactivity in the reaction tube. The release of labeled fibrin degradation products, expressed in percent, was plotted versus time.

Figure 11:
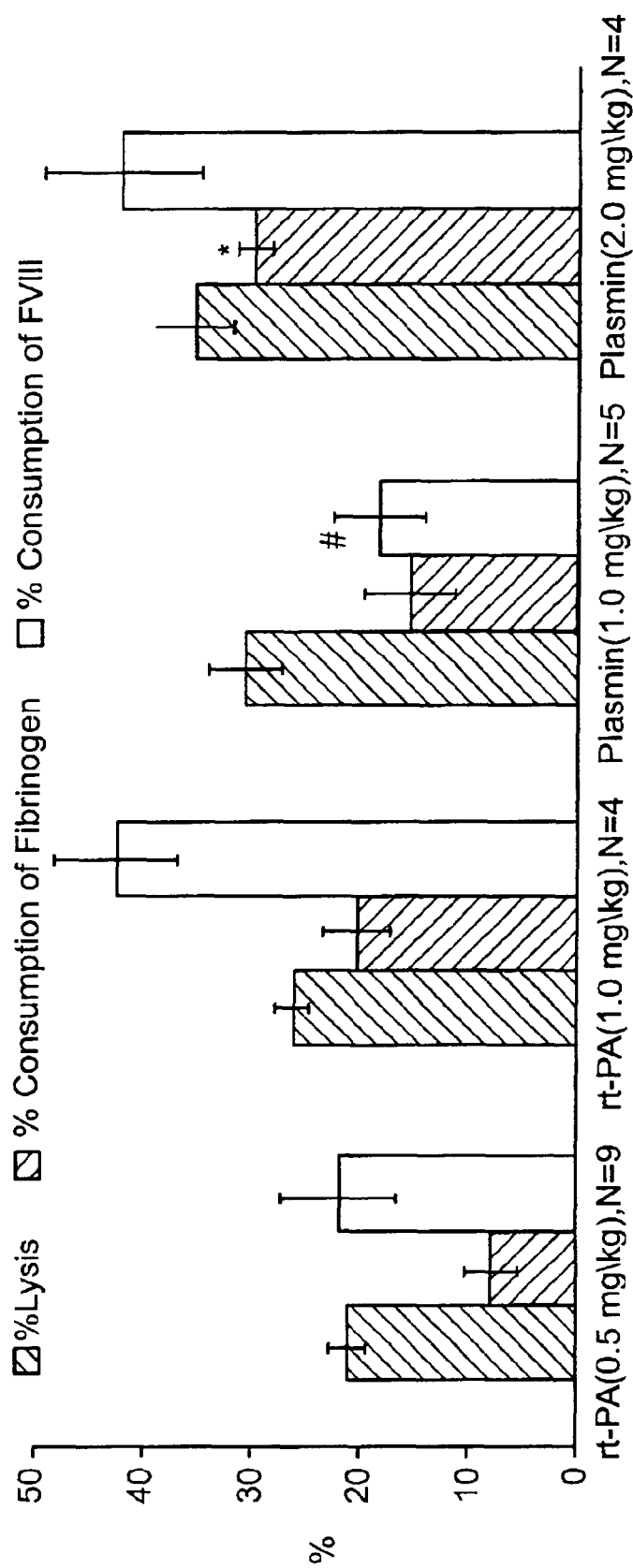
FIG. 11 compares local administration of tPA and plasmin on thrombus lysis, and Factor VIII and fibrinogen consumption, at 60 minutes.
Figure 12:
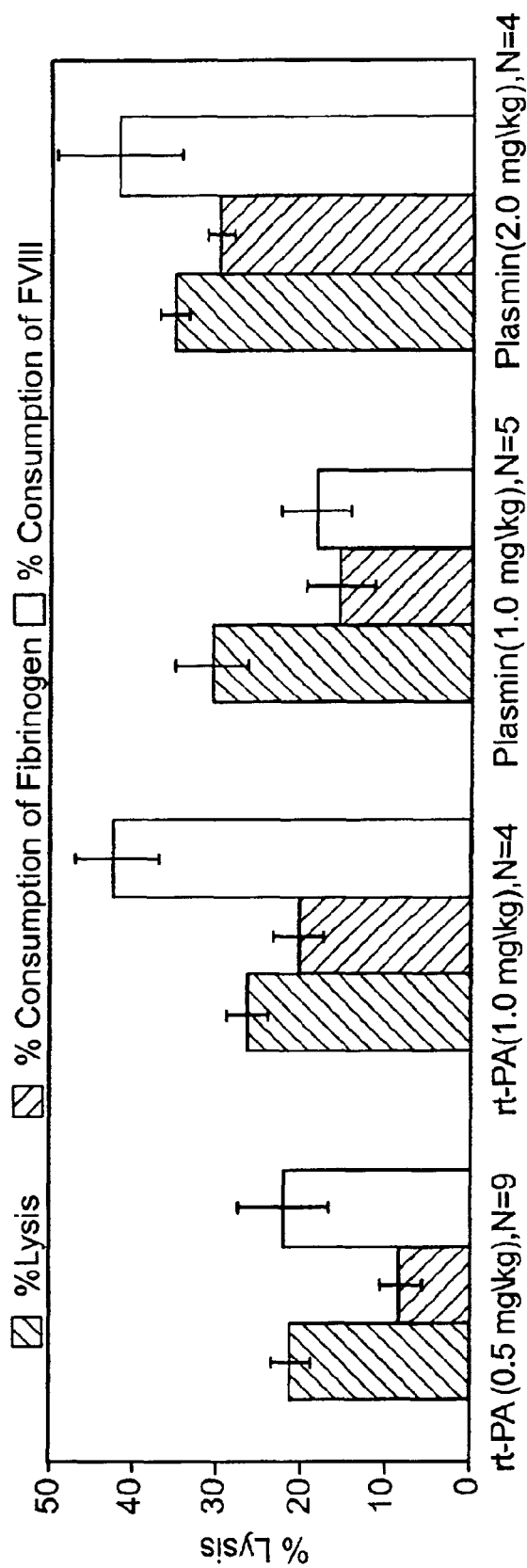
FIG. 12 compares local administration of tPA and plasmin on thrombus lysis at 90 minutes, and Factor VIII and fibrinogen consumption at 60 minutes.

The percent lysis of radiolabeled thrombi and consumption of Factor VIII and fibrinogen are shown at 60 minutes (FIG. 11) and 90 minutes incubation periods (FIG. 12). At 0.5 mg/kg and 1.0 mg/kg, tPA induced 16±2% and 21±2% lysis, respectively, whereas plasmin at 1.0 mg/kg and 2.0 mg/kg induced 26±3% and 33±4% lysis, respectively. At 90 minutes, tPA infusion had resulted in 21±2% and 26±2% lysis, respectively, compared to plasmin which induced lysis of 31±4% and 36±2%, respectively.

EXAMPLE 13

Risk/benefit Assessment of Plasmin Treatment vs tPA Treatment.

An extensive comparative pharmacological evaluation (risk/benefit) of plasmin in the rabbit model of thrombolysis was determined. The efficacy of plasmin was compared with that of tPA. Percent lysis and restoration of blood flow as indices of efficacy were used. These analysis were performed in separate experiments. The respective side effects induced by these thrombolytic agents were compared by measuring the consumption of Factor VIII and fibrinogen and assessing bleeding times. This allowed a determination of an approximate risk/benefit profile.

Figure 13:
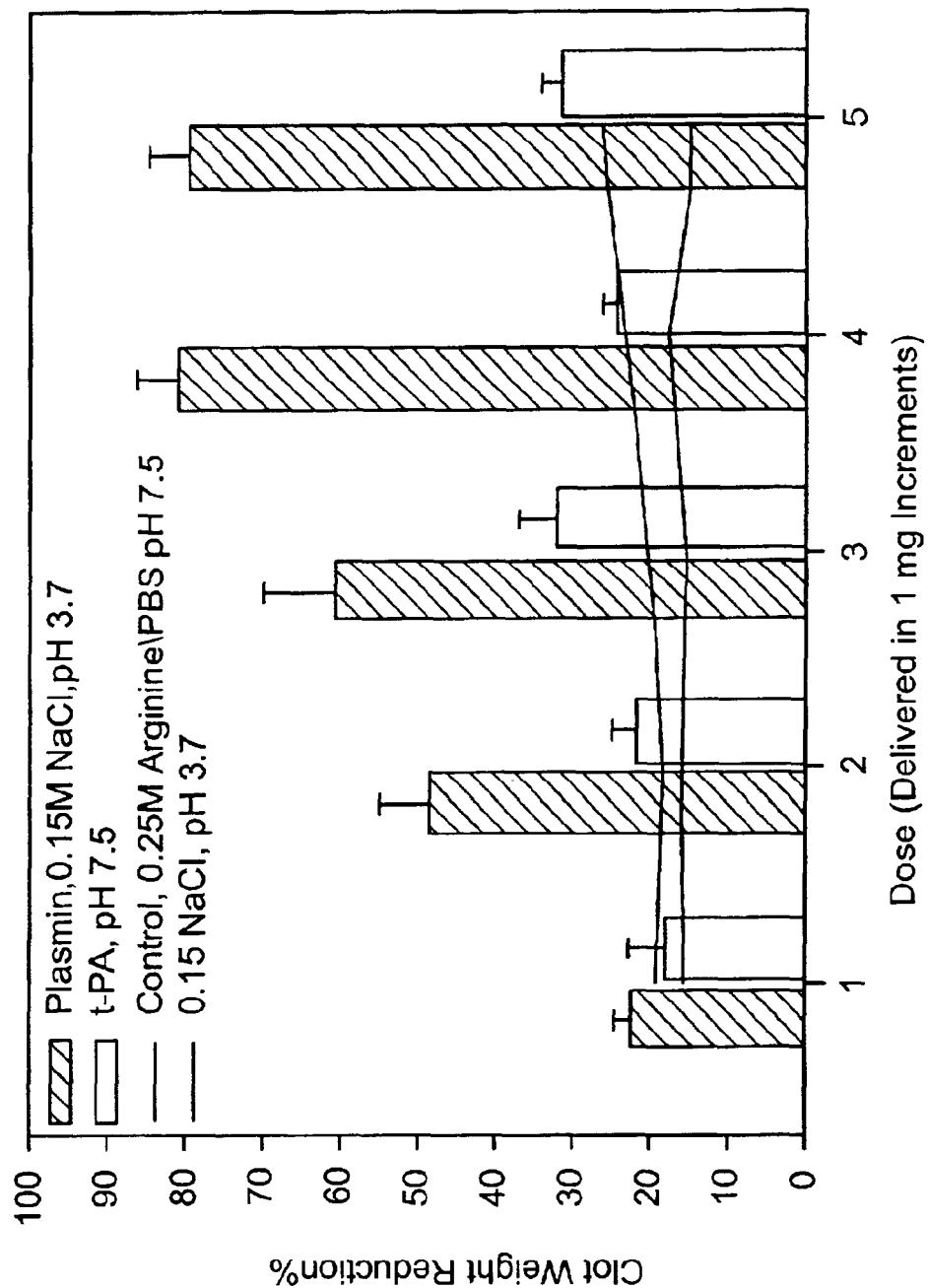
FIG. 13 illustrates the extent of clot lysis by tPA and reversibly inactivated acidified plasmin as a PAO model.

To determine the risk profile, the $ED_{50}$ dose for tPA was calculated, using the consumption of Factor VIII as a surrogate marker for induction of the lytic state and bleeding. The consumption of Factor VIII was directly related to the bleeding side effect by replenishing back Factor VIII (Kogenatee) and returning normal hemostasis. tPA doses ranging from 0.1 mg/kg to 3.0 mg/kg with a N of at least 10 animals/dose were examined. 1.0 mg/kg is considered a clinical dose for tPA. The calculated $ED_{50}$ for tPA was 1.8 mg/kg. A similar calculation for locally administered plasmin gave an $ED_{50}$ of 3.6 mg/kg. Therefore, twice the dose of plasmin (wt basis) induced similar bleeding side effects as tPA. The efficacy (% lysis and blood flow) with doses of tPA and plasmin with equivalent risk profiles i.e., consumption of coagulation proteins and bleeding were evaluated as shown in FIG. 13. At all equivalent risk doses tested, tPA (0.5–3.0 mg/kg) and plasmin (1.0–3.0 mg/kg), plasmin induced at least similar or significantly better rates of lysis and restoration of blood flow compared to tPA. The pharmacological data, therefore, is sufficient to recommend that plasmin be considered for the lytic treatment of thrombi accessible by catheter placement.

EXAMPLE 14

Degradation Peptides of Plasmin Samples Characterized by N-terminal Sequencing

Figure 14:
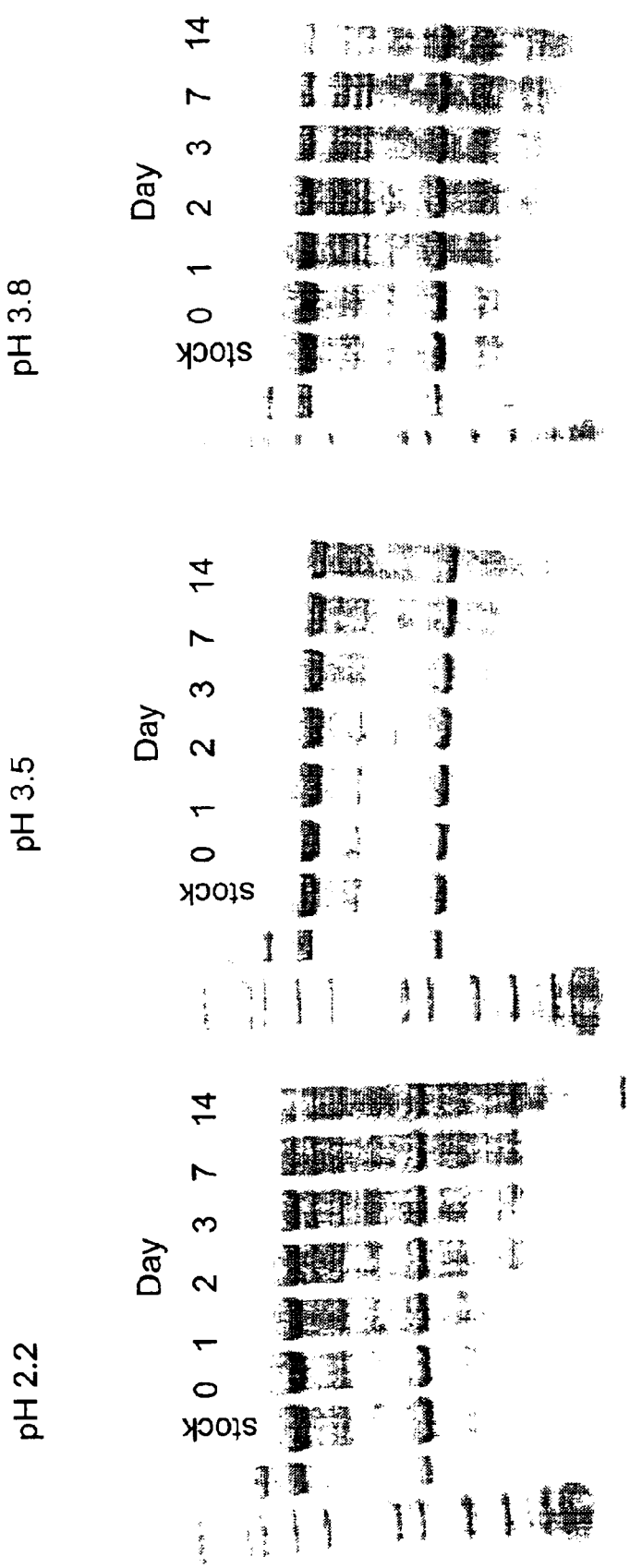
FIG. 14 illustrates the progressive degradation of a plasmin composition at a pH of 2.2, 3.5, or 3.7.

The degradation peptides of plasmin samples were characterized by N-terminal sequencing as follows. Plasmin compositions were formulated at low pH values: a pH less than 2.5 and a pH of 3.5 and 3.8 containing 2 mM acetic acid. The plasmin samples were analyzed using SDS-PAGE with 4–12% Bis-Tris NuPage gels, as shown in FIG. 14. The protein bands were transferred to a PVDF membrane, stained with Coomassie Blue R-250 (Bio-RAD Laboratories, Hercules, Calif.) and bands cut out using a scalpel.

N-terminal sequence analysis was performed directly from the membrane using a Hewlett Packard 241 Protein Sequencer (Hewlett Packard, Inc., Glen Allen, Va.). Ten cycles were run for each band so that the corresponding fragment of plasmin could be identified. Molecular weights for each band were determined with densitometry analysis using the Mark 12 marker available from Invitrogen, Inc. (San Diego, Calif.)

Figure 15:
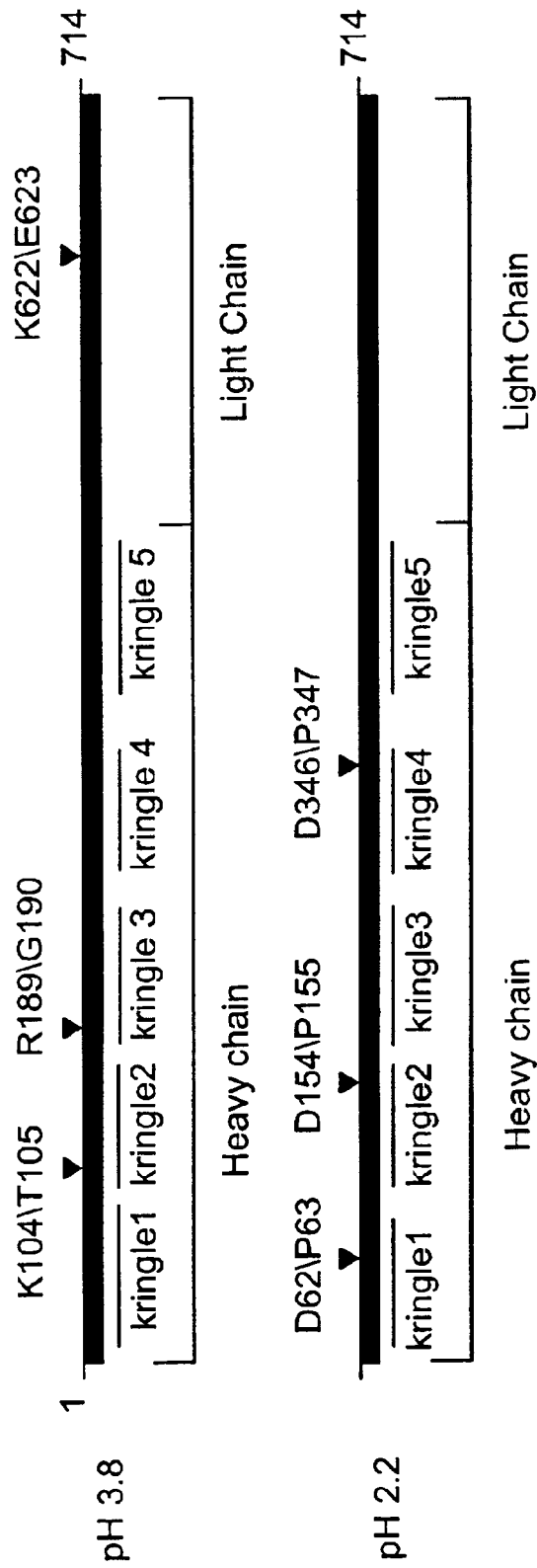
FIG. 15 illustrates the cleavage sites generated in plasmin at pH 2.2 and 3.8.

Three polypeptides generated by incubation of plasmin at pH 3.8 began at positions (numbering relative to Lys-plasmin) threonine (T105), glycine (G190) and glutamic acid (E623). From the known amino acid sequence of plasmin, it was determined that the first two polypeptides were from the heavy chain and the third from the light chain. As shown in FIG. 15, the amino acid preceding the N-terminal amino acid was either arginine or lysine (K104, R189, and K622). It is commonly known that plasmin cleaves proteins on the carboxyl side of lysine and arginine. These results demonstrated that compositions of plasmin at pH 3.8 were susceptible to autodegradation.

Three polypeptides generated by incubation of plasmin at pH 2.2 began with proline at the N-termini. From the known amino acid sequence of plasmin, it was determined that these polypeptides were from the heavy chain, starting at positions P63, P155, and P347, as shown in FIG. 15. The amino acid preceding each proline was an aspartic acid (D62, D154, and D346). It is commonly known that aspartyl-prolyl (D-P) peptide bonds are acid labile. These results demonstrated that compositions of plasmin at pH 2.2 were susceptible to acid hydrolysis of peptide bonds.

EXAMPLE 15

Sugars in Low pH Formulation Stabilize Plasmin

Plasmin was formulated in one of the following acids with at least one of the following sugars, at pH 2.5 to 4.0. The group of acids included 1 mM to 500 mM of acetic acid, citric acid, serine, threonine, isoleucine, valine, glutamine, P-alanine, or other acids, preferable in the range of 1 mM to 50 mM. The group of sugars included 0.2% to 20% of maltose, mannitol, sorbitol, sucrose, lactose, glucose and trehalose. The plasmin formulation without any excipient was included as a control. All samples were incubated at 37° C. for 7 days. The change in plasmin integrity was analyzed by running reducing SDS-PAGE.

Figure 16:
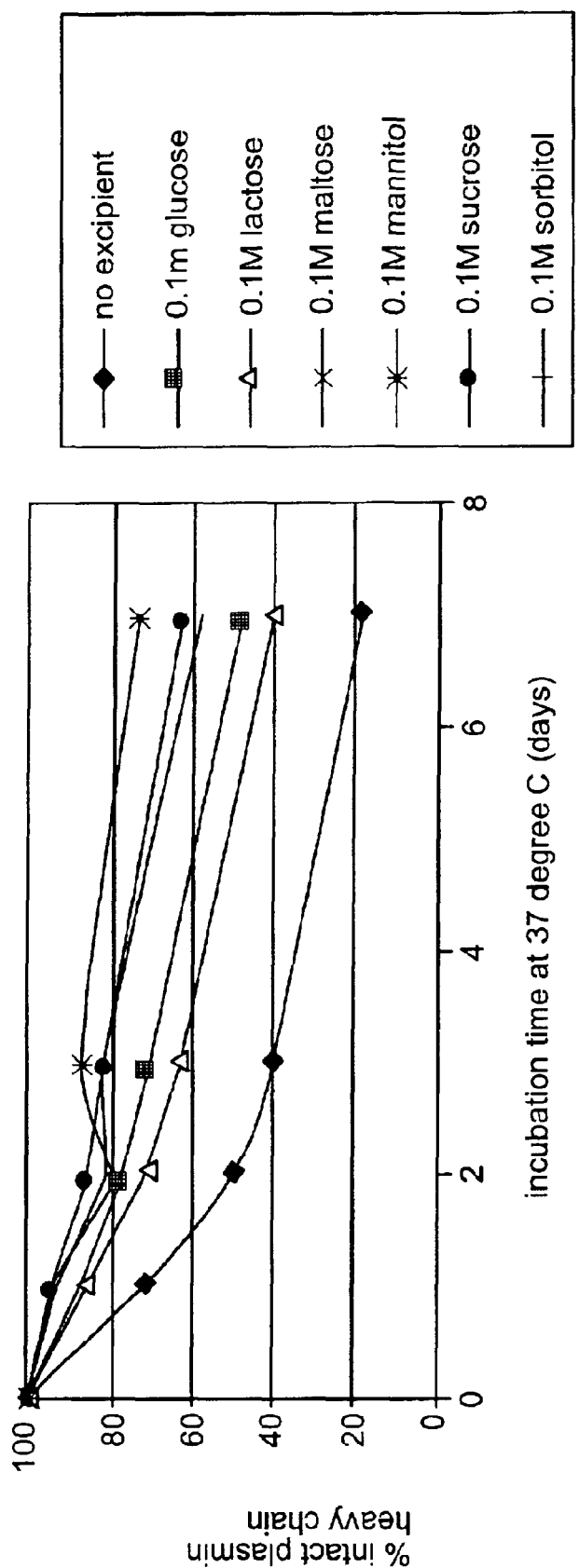
FIG. 16 illustrates the stability at 37° C. of a reversibly inactivated acidified plasmin at pH of 3.7, with carbohydrate stabilizers.

The results shown in FIG. 16 demonstrate that sugars have a stabilizing effect on plasmin at pH 3.5 and improve the benefits from storing reversibly inactivated acidified plasmin at low pH.

EXAMPLE 16

Figure 17:
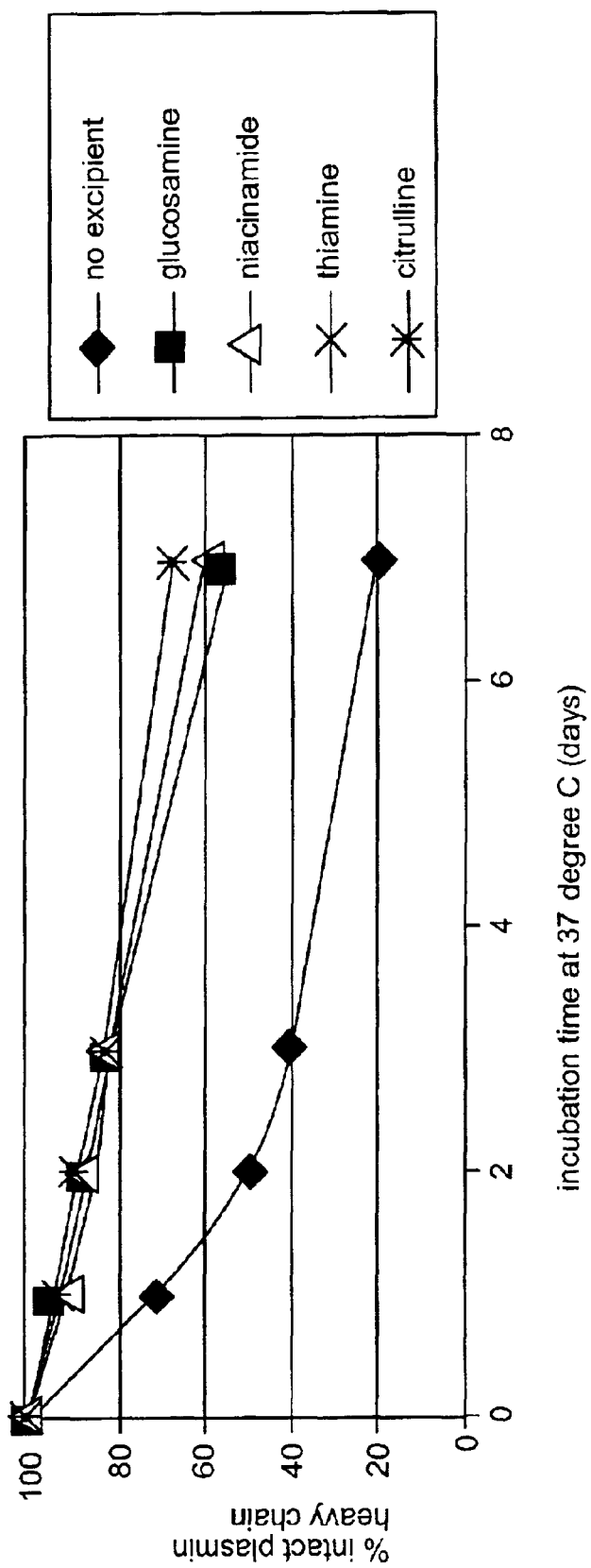
FIG. 17 illustrates the stability at 37° C. of a reversibly inactivated acidified plasmin at a pH of 3.7 with glucosamine, niacinamide, thiamine or citrulline as a stabilizing agent.

Stabilization of Reversibly Inactivated Acidified Plasmin Composition with Non-carbohydrate Stabilizing Agents Reversibly inactivated acidified compositions were formulated at 1 mg/ml in 5 mM acetic acid, pH 3.7, according to the present invention, with 0.1M of glucosamine, niacinamide, citrulline or thiamine added as a non-carbohydrate stabilizer. A reversibly inactivated acidified plasmin formulation without any excipient stabilizing agent was included as a control. All samples were incubated at 37° C. for 7 days and the change in plasmin integrity analyzed using SDS-PAGE under non-reducing conditions. Referring now to FIG. 17, all of the non-sugar stabilizing agents tested improved the stability of the reversibly inactivated acidified plasmin composition at 37° C. over the 7day test period.

A reversibly inactivated acidified plasmin compositions was also formulated at 1 mg/ml in 2 mM acetic acid, pH 3.4, according to the present invention, with 150 mM sodium chloride as a stabilizing agent. The same formulation, but without sodium chloride, was also prepared and included as a control. Samples were incubated at 4° C. for 28 days. The change in plasmin integrity was analyzed using SDS-PAGE under non-reducing conditions, as described in Example 3 above. Values were normalized relative to day 0 controls which were assigned a value of 100%. Table 5, the results demonstrate that plasmin stored at 4° C. is more stable in the low-pH formulation containing sodium chloride.

TABLE 5

Stability of reversibly inactivated acidified plasmin composition (2 mM NaAc, pH 3.4) with or without 150 mM sodium chloride, stored at 4° C.

| Sodium chloride Concentration (mM) | Plasmin (mg/ml) | % intact heavy chain after 28 days | % intact light chain after 28 days | % activity after 28 days |
|---|---|---|---|---|
| 0 | 1 | 90 | 93 | 81 |
| 150 | 1 | 101 | 95 | 97 |

EXAMPLE 17

Plasma Can Neutralize Proportionally Large Volumes of Acidified Saline

Figure 18:
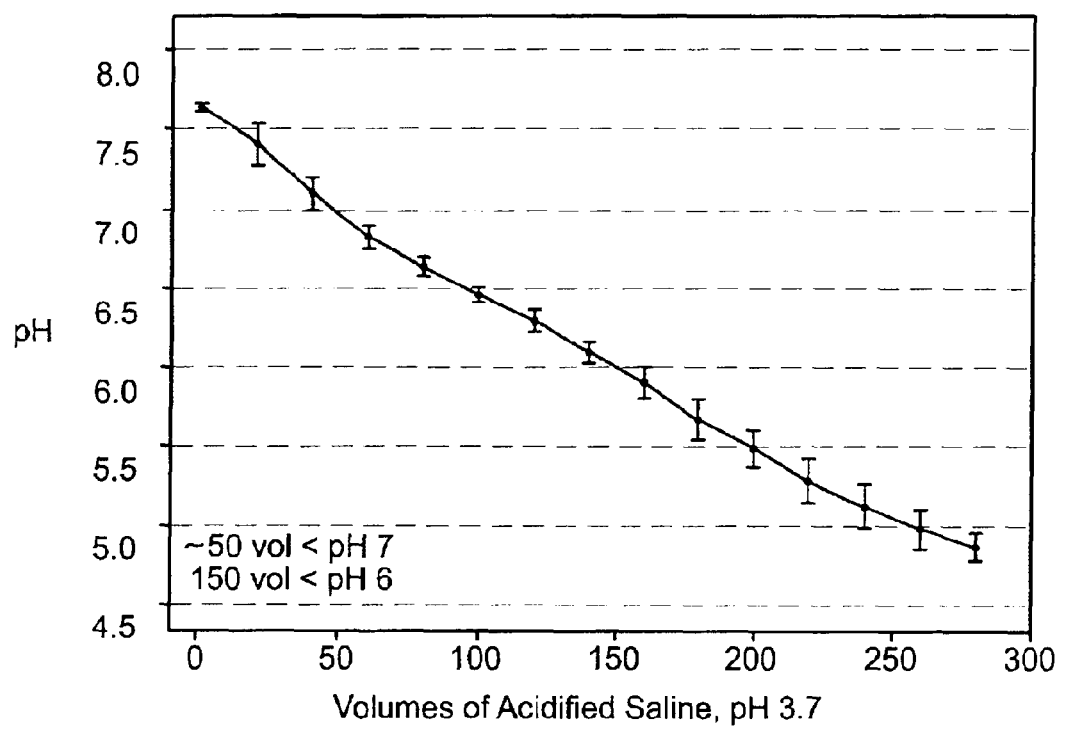
FIG. 18 illustrates the titration, with human serum, of plasmin solutions having various low buffering capacity buffers.

In order to estimate the volume of reversibly inactivated acidified plasmin compositions of the present invention that can be neutralized by one milliliter of serum at physiological pH, a series of titration experiments were performed. A 1-ml volume of serum is estimated to represent the liquid phase volume of an average retracted clot found in the artery of a PAO patient. Serum (1 ml) was titrated with an acidified (pH 3.7) low buffering capacity buffer solution typical of that in which reversibly inactivated acidified plasmin according to the present invention is formulated. As shown in FIG. 18, 1 ml of serum is capable of neutralizing approximately 150 ml of acidified saline. The latter volume will exceed the likely volume of reversibly inactivated acidified plasmin required for treatment of peripheral arterial occlusions.

Thus, the formulation of reversibly inactivated acidified plasmin in a low buffering capacity buffer provides the basis for an effective and stable pharmaceutical composition. Such compositions would allow administration of reversibly inactivated acidified plasmin at room temperature for the time required for treatment without the plasmin significantly losing potency during delivery of the preparation to the patient.

EXAMPLE 18

Trypsin Stabilized at Low pH Can be Reactivated by Transfer to Higher pH Environment Trypsin (16.4 mg, Sigma Chemical Co. Catalog No. T-1426) was dissolved in 2.28 ml of 50 mM Tris/0.5 M NaCl (pH 8.0). The trypsin solution was loaded onto a 1-ml column of Benzamidine-Sepharose (Pharmacia Code No. 17-0568-01) that had been pre-equilibrated with 50 mM Tris/0.5 M NaCl (pH 8.0). This column was washed with 4 ml of this latter buffer, resulting in a decrease in the eluate absorbance (280 nm) to less than 0.03. Trypsin was eluted from this column in an inactivated state with 0.5-ml volumes of 200 mM glycine/0.5 M NaCl (pH 3.0); the third through fifth 0.5-ml fractions eluted from this column contained the peak values of absorbance (280 nm) and were pooled. The absorbance (280 nm) of this pooled trypsin eluate was determined to be 9.22; based upon the extinction coefficient for trypsin ($E_{280}$ for a 1% solution=17.09) and the molecular weight of trypsin (24,000), the concentration of total trypsin protein in this pooled column eluate was calculated to be 225 $\mu$M.

The concentration of trypsin active sites in this pooled trypsin column eluate was determined by the method described by Case & Shaw, Biochem. Biophys. Res. Commun. 29, 508 (1967) and incorporated herein by reference in its entirety, using p-nitrophenylguanidinobenzoate as active-site titrant. This assay was performed at pH 8.3, by diluting a small volume (100 $\mu$l) of the pooled trypsin column eluate into an assay mixture also containing 700 $\mu$l of 50 mM sodium borate (pH 8.3), 200 $\mu$l of 10 mM sodium phosphate/ 1% glycine (pH 7.0) plus 10 $\mu$l of p-nitrophenylguanidininobenzoate (dissolved in dimethyl formamide); the final pH of this mixture composition was determined to be 8.3. The trypsin-dependent amount of p-nitrophenol formed in this assay was monitored at 410 nm. Based upon the extinction coefficient for p-nitrophenol at 410 nm and at pH 8.3 (16,595 $M^{-1}$), 100 $\mu$l of this pooled trypsin column eluate present in the 1.01-ml assay corresponded to a concentration of 22.95 $\mu$M trypsin active sites present in the cuvette. Therefore, the original stock solution of pooled trypsin column eluate contained 231 $\mu$M trypsin active sites. This latter value is identical, within experimental error, to the concentration of total trypsin protein present (225 $\mu$M). These results demonstrate that trypsin can be adjusted to low pH and then transferred to a higher pH environment with reactivation of its active site.

REFERENCES

The following references are specifically incorporated herein by reference:
- Deutsch, D. G. & Mertz, E. T., Science 170, 1095–1096. (1970)
- Robbins, K. C. & Summaria, L. Meth. Enzymol., 19, 257–273 (1970)
- Castellino, F. J. & Powell, JR. Meth. Enzymol., 80, 365–378.(1981)
- Lijnen, H. R., Zamarron, C., Blaber, M, Winkler, M. E. & Collen, D, J. Biol.Chem. 261, 1253–1258 (1986)
- Wiman, B., Biochem. Journal. 191(1):229–32(1980)
- Barrett, A. J., Brown, M. A., & Sayers, C. A., 181, 401–418 (1979)
- Collen, D, Stassen, J. M. & Verstraete, M., J. Clin. Invest. 71(2), 368–376 (1983)
- Marder, V. J., Shortell, C. K, Fitzpatrick, P. G., Kim, C. & Oxley, D. Thrombosis Res. 67, 31–40 (1992)
- U.S. Pat. Nos: 5,288,489 3,950,513 5,879,923.

What is claimed is:

1. A method of administering a therapeutic dose of a reversibly inactivated acidified mammalian serine protease composition to a human or animal having a thrombotic occlusion, comprising the steps of:
   a) identifying a human or animal having a thrombotic occlusion; and
   b) administering parenterally to the human or animal a therapeutic dose of a pharmaceutically acceptable reversibly inactivate acidified mammalian serine protease composition substantially free o plasminogen activator, wherein the therapeutic dose is delivered into or proximally to the thrombotic occlusion;
   wherein the mammalian serine protease composition comprises a low buffering capacity buffer and has a pH less than about 4.0,
and wherein the composition is a pharmaceutically acceptable solution that can be raised to a physiological pH by adding no more than about 5 volumes of serum to the solution relative to the volume of solution.

2. The method of claim 1, further comprising the step:
   c) allowing the administered mammalian serine protease composition to interact with the thrombotic occlusion.

3. The method of claim 2, further comprising the steps:
   d) monitoring the level of vascular flow of the human or animal; and
   e) repeating steps (a)–(d) until a pre-selected level of vascular flow is attained.

4. The method of claim 1, wherein the thrombotic occlusion is a vascular occlusion selected from a coronary thrombosis, deep venous thrombosis, peripheral thrombosis, embolic thrombosis, hepatic vein thrombosis, marasmic thrombosis, sinus thrombosis, venous thrombosis, an arterial thrombosis, an occluded arterio-venal shunt, or an occluded catheter device.

5. The method of claim 1, wherein the reversibly inactivated acidified mammalian serine protease composition is lyophilized, and wherein the method further comprises adding a pharmaceutically acceptable carrier to the lyophilized mammalian serine protease composition before administration to the human or animal.

6. The method of claim 1, wherein the reversibly inactivated acidified mammalian seine protease composition comprises Glu-plasmin, Lys-plasmin, mini-plasmin, micro-plasmin, or a truncated variant thereof.

7. The method of claim 1, wherein the reversibly inactivated acidified mammalian seine protease composition further comprises an anti-thrombotic agent.

8. The method of claim 1, wherein the low buffering capacity buffer comprises water and at least one pharmaceutically acceptable acid, wherein the acid is an organic acid selected from a carboxylic acid, an oligopeptide, an amino acid, or inorganic acid.

9. The method of claim 8, wherein the pharmaceutically acceptable acid is selected from formic acid, acetic acid, citric acid, glycine, isoleucine, serine, threonine, glutamine, aspartic acid, valine and alanine.

10. The method of claim 8, wherein the pharmaceutically acceptable acid is acetic acid or citric acid.

11. The method of claim 8, wherein the pharmaceutically acceptable acid is acetic acid.

12. The method of claim 1, wherein the reversibly inactivated acidified mammalian serine protease composition has a pH of between about 2.5 and about 4.0.

13. The method of claim 1, wherein the reversibly inactivated acidified mammalian serine protease composition has a pH of between about 3.0 and about 4.0.

14. The method of claim 1, wherein the reversibly inactivated acidified mammalian serine protease composition has a pH of between about 3.1 and about 3.5.

15. The method of claim 7, wherein the mammalian serine protease is in a concentration range of between about 0.01 mg/ml to about 50 mg/ml.

16. The method of claim 7, wherein the mammalian serine protease is in a concentration range of between about 0.1 mg/ml to about 10 mg/ml.

17. The method of claim 8, wherein the acid is in a concentration range of between about 1 mM to about 500 mM.

18. The method of claim 8, wherein the acid is in a concentration range of between about 1 mM and 50 mM.

19. The method of claim 1, wherein the reversibly inactivated acidified mammalian serine protease composition further comprises a stabilizing agent.

20. The method of claim 19, wherein the stabilizing agent is a pharmaceutically acceptable carbohydrate selected from glucose, maltose, mannitol, sorbitol, sucrose, lactose or trehalose.

21. The method of claim 20, wherein the carbohydrate has a concentration in a range of about 0.2% w/v to about 20% w/v.

22. The method of claim 20, wherein the carbohydrate is glucose and the concentration thereof is about 20%.

23. The method of claim 20, wherein the stabilizing agent is selected from glucosamine, niacinamide and thiamine.

24. The method of claim 20, wherein the stabilizing agent has a concentration in the range of about 0.01M to about 0.1M.

25. The method of claim 1, wherein the therapeutic dose of the reversibly inactivated acidified mammalian serine protease composition is in a range of between about 0.1 mg plasmin/kg body weight and 10.0 mg plasmin/kg body weight.

26. The method of claim 1, wherein the therapeutic dose of the reversibly inactivated acidified mammalian serine protease composition is in a range of between about 0.2 mg plasmin/kg body weight and 4.0 mg plasmin/kg body weight.

27. The method of claim 1, wherein the therapeutic dose of the reversibly inactivated acidified mammalian serine protease composition is in a range of between about 1.0 mg plasmin/kg body weight and 2.0 mg plasmin/kg body weight.

28. The method of claim 1, wherein the reversibly inactivated acidified mammalian serine protease composition is administered by a catheter device.

29. The method of claim 28, wherein the catheter device is directed to a vascular occlusion.

30. The method of claim 29, wherein the catheter device delivers the reversibly inactivated acidified mammalian serine protease composition proximal to, or into, a thrombotic occlusion.

31. The method of claim 29, wherein the catheter device enters the thrombotic occlusion and the catheter delivers the reversibly inactivated acidified mammalian serine protease composition directly into the thrombotic occlusion.

32. The method of claim 1, wherein the solution can be raised to physiological pH by adding no more than about 1 volume of serum to the solution relative to the volume of solution.

33. The method of claim 1, wherein the solution can be raised to physiological pH by adding no more than about 0.7 volumes of serum to the solution relative to the volume of solution.

34. The method of claim 1, wherein the solution can be raised to physiological pH by adding no more than about 0.3 volumes of serum to the solution relative to the volume of solution.

35. The method of claim 1, wherein the solution can be raised to physiological pH by adding no more than about 0.1 volumes of serum to the solution relative to the volume of solution.

* * * * *

UNITED STATES PATENT AND TRADEMARK OFFICE
CERTIFICATE OF CORRECTION

| | |
|---|---|
| PATENT NO. | : 6,964,764 B2 |
| APPLICATION NO. | : 10/143157 |
| DATED | : November 15, 2005 |
| INVENTOR(S) | : Zimmerman et al. |

It is certified that error appears in the above-identified patent and that said Letters Patent is hereby corrected as shown below:

Column 1, Line 8 should read, --PCT/US00/31115 published in English on May 25, 2001--

Signed and Sealed this

Eleventh Day of December, 2007

JON W. DUDAS
*Director of the United States Patent and Trademark Office*

(12) EX PARTE REEXAMINATION CERTIFICATE (7691st)
United States Patent
Zimmerman et al.

(10) Number: US 6,964,764 C1
(45) Certificate Issued: Aug. 17, 2010

(54) METHOD OF THROMBOLYSIS BY LOCAL DELIVERY OF REVERSIBLY INACTIVATED ACIDIFIED PLASMIN

(75) Inventors: Thomas P. Zimmerman, Raleigh, NC (US); Valery Novokhatny, Raleigh, NC (US); Kyle A. Landskroner, Mill Valley, CA (US); Gary J. Jesmok, Richmond, CA (US); Kathryn K. Taylor, Apex, NC (US)

(73) Assignee: Morgan Stanley Senior Funding, Inc., as the Administrative Agent, New York, NY (US)

Reexamination Request:
No. 90/010,619, Jul. 28, 2009

Reexamination Certificate for:
Patent No.: 6,964,764
Issued: Nov. 15, 2005
Appl. No.: 10/143,157
Filed: May 10, 2002

Certificate of Correction issued Dec. 11, 2007.

Related U.S. Application Data

(63) Continuation of application No. PCT/US00/31115, filed on Nov. 13, 2000, which is a continuation-in-part of application No. 09/438,331, filed on Nov. 13, 1999, now Pat. No. 6,355,243.

(51) Int. Cl.
| | |
|---|---|
| *A61K 47/18* | (2006.01) |
| *A61K 38/43* | (2006.01) |
| *A61K 38/00* | (2006.01) |
| *A61K 47/02* | (2006.01) |
| *A61K 38/48* | (2006.01) |
| *A61K 47/12* | (2006.01) |
| *A61K 47/16* | (2006.01) |
| *A61K 47/26* | (2006.01) |
| *C12N 9/68* | (2006.01) |

(52) U.S. Cl. .................. 424/94.64; 435/215; 435/217
(58) Field of Classification Search ................ None
See application file for complete search history.

(56) References Cited

U.S. PATENT DOCUMENTS

| | | | |
|---|---|---|---|
| 3,950,223 | A | 4/1976 | Yugari et al. |
| 3,950,513 | A | 4/1976 | Jensen |
| 4,418,052 | A | 11/1983 | Wong |
| 4,462,980 | A | 7/1984 | Diedrichsen et al. |
| 4,499,073 | A | 2/1985 | Tenold |
| 5,068,106 | A | 11/1991 | Paques et al. |
| 5,112,609 | A | 5/1992 | Johnston et al. |
| 5,407,678 | A | 4/1995 | Rose et al. |
| 5,587,291 | A | 12/1996 | Binder |
| 6,479,253 | B1 | 11/2002 | Silver et al. |

FOREIGN PATENT DOCUMENTS

| | | |
|---|---|---|
| DE | 3617753 A1 | 12/1986 |
| EP | 0256836 A1 | 2/1988 |
| EP | 0297294 A1 | 1/1989 |
| GB | 985498 | 3/1965 |
| GB | 2 090 599 A | 7/1982 |
| WO | WO 97/15572 | 5/1997 |
| WO | WO 98/37086 A1 | 8/1998 |

OTHER PUBLICATIONS

Aronen, H.J. et al., "99mTc–plasmin test in deep vein thrombosis of the leg," Eur J Nucl Med, 10:10–12 (1985).

Browse, N., "Deep Vein Thrombosis," British Medical Journal, 4:676–678 (1969).

Burnouf–Radosevich et al., "Nanofiltration, A New Specific Virus Elimination Method Applied to High–Purity Factor IX and Factor XI Concentrates," Vox Sang, 67(2):132–138 (1994).

Dahl, O.E., et al., "99mTc–Plasmin Uptake Test is Unreliable for Diagnosing Asymptomatic Deep Vein Thrombosis After Hip Replacement Surgery," Thrombosis Research, 62:781–784 (1991).

Decision of the Board of Patent Appeals and Interferences dated Feb. 19, 2008 in Appeal No. 2007–0545, Exparte Thomas P. Zimmerman, Valery Novokhatny, Shang Jiang and James Colancleve (with claims considered on Appeal).

Edenbrandt, C.M., et al., "Return to normal of 99mTc–plasmin test after deep venous thrombosis and its relationship to vessel wall fibrinolysis," Eur J Nucl Med 12:197–200 (1986).

Edenbrandt, C.M., et al., "Comparison between 99Tcm–porcine plasmin and 99Tcm–labelled erythrocytes in diagnosis of deep vein thrombosis," Clinical Physiology 4:243–252 (1984).

Edenbrandt, C.M., et al., "Diagnosis of Deep Venous Thrombosis by 99mTc–Human Serum Albumin Microcolloid," Eur J Nucl Med 8:332–334 (1983).

Edenbrandt, C.M., et al., "Follow–up of circulatory changes secondary to deep venous thrombosis with special regards to radionuclide tests," Clinical Physiology 6:153–161 (1986).

GE Healthcare—Affinity chromatography, Benzamidine Sepharose 4 Fast Flow (high sub) HiTrap Benzamidine FF (high sub) (Data File 18–1139–38 AC—first published Sep. 2000).

(Continued)

*Primary Examiner*—Bruce Campell

(57) ABSTRACT

Methods of thrombolysis that allow the use of a fibrinolytic composition comprising reversibly inactivated acidified plasmin and the localized delivery of the plasmin to a vascular thrombotic occlusion are disclosed. Further disclosed is a method for administering a therapeutic dose of a fibrinolytic composition substantially free of plasminogen activator to a human or animal having a vascular thrombotic occlusion. The fibrinolytic composition includes a reversibly inactivated acidified plasmin substantially free of plasminogen activator. Intravascular catheter delivery of the fibrinolytic composition directly into or in the immediate vicinity of the thrombus is disclosed to minimize the systemic degradation of fibrin while retaining the maximum plasmin activity against the thrombus.

OTHER PUBLICATIONS

Ito et al., "Separation of Human Glu–Plasminogen, Lys–Plasminogen and Plasmin by High–Performance Affinity Chromatography on Asahipak GS Gel Coupled with p–Aminobenzamidine," Journal of Chromatography, 348:199–204 (1985).

Knight, L.C., "Radiopharmaceuticals for Thrombus Detection," Seminars in Nuclear Medicine, 20(1):52–67 (1990).

Lagerstedt, C., et al., "99mTc plasmin in 394 consecutive patients with suspected deep venous thrombosis," Eur J Nucl Med, 15:771–775 (1989).

Marder, V.J., et al., "Plasmin Induces Local Thrombolysis without Causing Hemorrhage: A Comparison with Tissue Plasminogen Activator in the Rabbit," Thromb Haemost, 86:739–745 (2001).

Martin, L., Pulmonary Physiology in Clinical Practice, The Essentials for Patent Care and Evaluation, The C.V. Mosby Company, Washington, D.C., Chapter 7, "Acid–base balance," pp. 129–146 (1987).

Milne, R.M., et al., "Postoperative Deep Venous Thrombosis: A Comparison of Diagnostic Techniques," Lancet, 2 (7722):445–447 (1971).

Owunwanne, A., et al., "Technetium Tc 99m plasmin in the diagnosis of inflammatory disease," Eur J Nucl Med, 12:496–499 (1987).

Perrson, B. and Darte, L., "Labeling Plasmin with Technetium–99m for Scintigraphic Localization of Thrombi," International Journal of Applied Radiation and Isotopes, 28:97–104 (1977).

Rasmussen, A., et al., "Distinction by Radioisotope Technique of a Subgroup with Increased Thrombophilic Potential among Patients Submitted to Major Abdominal Surgery," Journal of Medicine, 17(5–6):357–364 (1986).

Sakata, Y., et al., "Differential binding of plasminogen to crosslinked and noncrosslinked fibrins: its significance in hemostatic defect in factor XIII deficiency," Blood, 63:1393–1401 (1984).

Suenson, E. and Thorsen, S., "Secondary–site binding of Glu–plasmin, Lys–plasmin and miniplasmin to fibrin," Biochem. J., 197:619–628 (1981).

Tengborn, L., et al., "Demonstration of 99m–Tc–Labelled Plasmin on the Surface of Ex Vivo Thrombi," Thrombosis Research, 28:783–791 (1982).

Vall, Z. and Patthy, L., "The Fibrin–binding Site of Human Plasminogen," Journal of Biological Chemistry, 269 (22):13690–13694 (1984).

Walker, B. and Lynas, J., "Review: Strategies for the inhibition of serine proteases," CMLS, Cell. Mol. Life Sci., 58:596–624 (2001).

Alkjaersig, N., et al., "The Activation of Human Plasminogen," J. Biol. Chem., 233(1): 81–85 (1958).

Alkjaersig, N., et al., "The Mechanism of Clot Dissolution by Plasmin," J. Clin. Invest., 38(7): 1086–1095 (1959).

Becker, Gary J., "Local Thrombolytic Therapy: Bridging the 'Generation Gap,'" Am. J. Roentgenol., 140(2): 403–405 (1983).

Holmberg, L., et al., "Purification of Urokinase by Affinity Chromatography," Biochim. Biophys. Acta., 445: 215–222 (1976).

Mathey D.G., et al., "Intravenous Urokinase in Acute Myocardial Infarction," Am. J. Cardiol., 55:878–882 (1985).

Ouellette, "Introduction to General, Organic, and Biological Chemistry," Second Edition (1988). The Ohio State University. Macmillan Publishing Company, New York, NY, pp. 288–290.

Petitpretz, P., et al., "Effects of a single bolus of urokinase in patients with life–threatening pulmonary emboli: a descriptive trial," Circulation, 70(5): 861–866 (1984).

Seifert, V., et al., "Efficacy of Single Intracisternal Bolus Injection of Recombinant Tissue Plasminogen Activator to Prevent Delayed Cerebral Vasospasm after Experimental Subarachnoid Hemorrhage," Neurosurgery, 25(4): 590–598 (1989).

Wiman, B., and Per Wallén, "Activation of Human Plasminogen by an Insoluble Derivative of Urokinase Structural Changes of Plasminogen in the course of Activation to Plasmin and Demonstration of a Possible Intermediate Compound," Eur. J. Biochem., 36(1): 25–31 (1973).

http://www.lakesidepress.com/pulmonary/books/physiology/chap7_1.htm, Chapter 7: Acid–Base Balance.

Extended European Search Report (EP 1 956 082 A1, dated Jul. 10, 2008).

Abe, et al., "Immobilized urokinase column as part of a specific detection system for plasminogen species separated by high–performance affinity chromatography," J. Chromatography, (1991), vol. 565, pp. 183–195.

Ambrus, et al., "Clinical and experimental studies on fibrinolytic enzymes," Ann NY Acad Sci., (Aug. 30, 1957), vol. 68, No. 1, pp. 97–137.

Amor, M., et al., "Thrombectomy with the hydrolysing catheter," Archives des Maladies du Couer et des Vaisseaux, (1997), vol. 90, No. 6, pp. 797–804.

Amris, et al., "Clinical studies on an activator free porcine plasma (plasmin–novo)," Sangre 9 (BARC), (1964), vol. 61, pp. 12–18.

Barth, K.H. et al., "Multicenter prospective randomized comparison between a mechanical thrombectomy systems (OASIS) and pule–spray thrombolysis for thrombosed hemodialysis grafts," Radiology, (Nov. 1998) vol. 209P, Supp. [S]: 714.

Bookstein, J.J., et al., How I Do It: "Pulse–spray pharmacomechanical thrombolysis," Cardiovasc. Intervent Radiol., (1992) vol. 15, pp. 228–233.

Freitag et al., "Lys–plasminogen as an adjunct to local intra–arterial fibrinolysis for carotid territory stroke: laboratory and clinical findings," Neuroradiology 38: 181–185 (1996).

Greig, et al., "Protamine–Heparin complex as a substrate For plasmin," Biochim. Biophys, Acia., (1963), vol. 67, pp. 658–668.

IX. Plasmin, In "Plarmaceutical Enzymes" (eds. R. Ruyssen & A. Lauwers)–Story Scientia, Gent, Belgium, (1978), pp. 123–131.

Lazzaro, C.R. et al., "Modified use of the arrow–trerotola percutaneous thrombolytic device for the treatment of trambosed hemodialysis access grafts[1]," J. Vasc. Inter Radiol, (Sep. 1999), vol. 10, No. 8, pp. 1025–1031.

Schmer, "The purification of bovine thrombin by affinity chromatography on benzamidine–agarose," Hoppe Seyler's Z Physiol Chem., (May 1972), vol. 353, pp. 810–814.

Shi, et al., "Differential autolysis of human plasmin at various pH levels," Thrombosis Research, 1988, vol. 51, pp. 355–364.

Shimura, et al., "High–performance affinity chromatography of plasmin and plasminogen on a hydrophilic vinyl–polymer gel coupled with p–aminobenzamidine," J. Chromatography, (1984), vol. 292, pp. 369–382.

S. Husain, "A single–step separation of the one–and two–chain forms of tissue plasminogen activator[1]," Arch Biochem Biophys., (1991), vol. 285, pp. 373–376.

Uflacker R, et al., "Treatment of thrombosed dialysis access grafts: Randomized trial of surgical thrombectomy versus mechanical thrombectomy with the amplatz device[1]," JVIR, (1996), vol. 7, No. 2, pp. 185–192.

Whisenant, B. K., et al., "Rheolytic thrombectomy with the possis AngioJet®: Technical considerations and initial clinical experience," J. of Invasive Cardiology, vol. 11, No. 7, (Jul. 1999), pp. 421–426.

Zeit, R.M., "Arterial and venous embolization: Declotting of dialysis shunts by direct injection of streptokinase[1]," Radiology, (1986), vol. 159, No. 3, pp. 639–641.

Walker, B., et al., "Strategies for the inhibition of serine proteases," CMLS. Cell. Mol. Life Sci., vol. 58, (2001), pp. 596–624.

Deacon et al, "Technetium 99m–plasmin: a new test for the detection of deep vein thrombosis", British Journal of Radiology (1980) 33, 673–677.

Segel (*Biochemical Calculations, How to Solve Mathematical Problems in General Biochemistry,* Second Edition, John Wiley & Sons, Inc., NY, NY 1976, pp. 83–85.

Owunwanne et al ("Technetium Tc 99m plasmin in the diagnosis of inflammatory disease", Eur J. Nucl Med (1987) 12:496–499.

Sembra et al "Iliofemoral Deep Venous Thrombosis: Aggressive Therapy with Catheter–directed Thrombolysis", Radiology 1994; 191:487–494.

Robbins et al, "Purification of Human Plasminogen and Plasmin by Gel Filtration on Sephadex and Chromotography on Diethylaminoethyl–sephadex", JBC, vol. 238, No. 3, pp. 952–962 (1963).

Decision of the Board of Patent Appeals and Interferences dated Feb. 19, 2008 in Appeal No. 2007–0545, Ex parte Thomas P. Zimmerman, Valery Novokhatny, Shang Jiang and James Colancleve (with claims considered on Appeal).

Martin *Pulmonary Physiology in Clinical Practice, The Essentials for Patient Care and Evaluation* The C.V. Mosby Company, Washington, D.C., 1987, Chapter 7, "Acid–base balance", pp. 129–146.

Novokhatny et al, "Thrombolytic potency of acid–stabilized plasmin: superiority over tissue–type plasminogen activator in an in vitro model of catheter–assisted thrombolysis" Journal of Thrombosis and Haemostasis, 1:1034–1041 (2003).

Amris et al., "Infusion of Porcine Plasmin in Man, Studies on Toxicology and Pharmacodynamics", Scandinav. J. Clin. & Lab. Investigation 179–188, 15, 1963.

US 6,964,764 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-35, dependent on an amended claim, are determined to be patentable.

New claim 36 is added and determined to be patentable.

1. A method of [administering a therapeutic dose of a reversibly inactivated acidified mammalian serine protease composition to a human or animal having a thrombotic occlusion] *treating a human or animal having a thrombotic occlusion*, comprising the steps of:
   identifying a human or animal having a thrombotic occlusion; and
   administering parenterally to the human or animal a therapeutic dose of a pharmaceutically acceptable reversibly inactivated acidified mammalian serine protease composition substantially free of plasminogen activator, wherein the therapeutic dose is delivered into or proximally to the thrombotic occlusion;
   wherein the mammalian serine protease composition comprises a low buffering capacity buffer and has a pH less than about 4.0,
   and wherein the composition is a pharmaceutically acceptable solution that can be raised to a physiological pH by adding no more than about 5 volumes of serum to the solution relative to the volume of solution.

36. *A method of administering a therapeutic dose of a reversibly inactivated acidified plasmin composition to a human or animal having a thrombotic occlusion, comprising the steps of:*
   *a) identifying a human or animal having a thrombotic occlusion; and*
   *b) administering parenterally to the human or animal a therapeutic dose of a reversibly inactivated acidified plasmin composition substantially free of plasminogen activator, wherein the therapeutic dose is delivered into or proximally to the thrombotic occlusion;*
   *wherein the reversibly inactivated, acidified plasmin composition comprises a low buffering capacity buffer and has a pH less than about 4.0,*
   *and wherein the reversibly inactivated acidified plasmin composition is a sterile solution that is suitable for pharmaceutical use directly without neutralization, including parenteral administration to humans, that can be raised to a physiological pH by adding no more than about 5 volumes of serum to the solution relative to the volume of solution.*

\* \* \* \* \*